US006641524B2

(12) United States Patent
Kovac

(10) Patent No.: US 6,641,524 B2
(45) Date of Patent: *Nov. 4, 2003

(54) SLING SYSTEM FOR TREATING INCONTINENCE

(75) Inventor: S. Robert Kovac, Kettering, OH (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/976,387

(22) Filed: Oct. 11, 2001

(65) Prior Publication Data

US 2002/0022841 A1 Feb. 21, 2002

Related U.S. Application Data

(63) Continuation of application No. 09/236,210, filed on Jan. 23, 1999, now Pat. No. 6,322,492, which is a continuation of application No. 09/111,525, filed on Jul. 8, 1998, now Pat. No. 6,039,686, which is a continuation-in-part of application No. 08/820,053, filed on Mar. 18, 1997, now abandoned.

(51) Int. Cl.$^7$ .......................... A61B 17/04; A61B 19/00
(52) U.S. Cl. ....................................................... 600/30
(58) Field of Search .............. 600/29, 30; 128/897–898, 128/885–887, DIG. 25; 606/232, 65, 67, 72, 73, 75; 623/12, 16

(56) References Cited

U.S. PATENT DOCUMENTS

| 2,738,790 A | | 3/1956 | Todt et al. | |
|---|---|---|---|---|
| 3,054,406 A | * | 9/1962 | Usher | .......................... 606/151 |
| 3,124,136 A | | 3/1964 | Usher | |

(List continued on next page.)

FOREIGN PATENT DOCUMENTS

| DE | 2305815 | 2/1973 |
|---|---|---|
| DE | 4220283 C2 | 5/1994 |
| EP | 0 047 308 A1 | 2/1992 |

(List continued on next page.)

OTHER PUBLICATIONS

Araki, Tohru et al., The Loop–Loosening Procedure for Urination Difficulties After Stamey Suspension of the Vesical Neck, The Journal of Urology, vol. 144, pp. 319–323 (Aug. 1990).

Asmussen, M. et. al., Simultaneous Urethro–Cystometry With a New Technique, Scand J Urol Nephrol 10, p. 7–11 (1976).

(List continued on next page.)

*Primary Examiner*—Samuel G. Gilbert
(74) *Attorney, Agent, or Firm*—Jeffrey J. Hohenshell

(57) ABSTRACT

A pubic bone-mounted urethra stabilization and support system and method therefor for the long term cure of recurrent female urinary incontinence. The system comprises, a pair of anchors affixed to the posterior/inferior pubic bone, sutures attach to the anchors and a mesh sling passing behind and about the urethra and the adjacent endopelvic fascia and having ends attached to the anchors by the anchor-mounted sutures. The method includes the steps of accessing said urethra with the endopelvic fascia therebehind and the pubic bone, properly locating and attaching the anchors to the pubic bone, properly locating the sling about the urethra and adjacent endopubic fascia and suturing and tensioning the ends of the sling to the anchors, causing said sling to restore, support and stabilize functional urethral continence anatomy and prevent urethral descent under intraabdominal pressure.

39 Claims, 12 Drawing Sheets

U.S. PATENT DOCUMENTS

| | | |
|---|---|---|
| 3,182,662 A | 5/1965 | Shirodkar |
| 3,384,073 A | 5/1968 | Van Winkle, Jr. |
| 3,580,313 A | 5/1971 | McKnight |
| 3,789,828 A | 2/1974 | Schulte |
| 3,995,619 A | 12/1976 | Glatzer |
| 4,172,458 A | 10/1979 | Pereyra |
| 4,246,660 A | 1/1981 | Wevers |
| 4,452,245 A * | 6/1984 | Usher .................... 606/151 |
| 4,509,516 A | 4/1985 | Richmond |
| 4,632,100 A | 12/1986 | Somers et al. |
| 4,857,041 A | 8/1989 | Annis et al. |
| 4,920,986 A | 5/1990 | Biswas |
| 4,938,760 A | 7/1990 | Burton et al. |
| 4,969,892 A | 11/1990 | Burton et al. |
| 4,979,956 A * | 12/1990 | Silvestrini ............ 623/13.11 |
| 5,007,894 A | 4/1991 | Enhorning |
| 5,012,822 A | 5/1991 | Schwarz |
| 5,013,292 A | 5/1991 | Lemay |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,188,636 A | 2/1993 | Fedotov |
| 5,256,133 A | 10/1993 | Spitz |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,383,904 A | 1/1995 | Totakura et al. |
| 5,386,836 A | 2/1995 | Biswas |
| 5,413,598 A | 5/1995 | Moreland |
| 5,439,467 A | 8/1995 | Benderev et al. |
| 5,520,700 A | 5/1996 | Beyar et al. |
| 5,544,664 A | 8/1996 | Benderev et al. |
| 5,562,689 A | 10/1996 | Green et al. |
| 5,571,139 A | 11/1996 | Jenkins, Jr. |
| 5,591,163 A | 1/1997 | Thompson |
| 5,611,515 A | 3/1997 | Benderev et al. |
| 5,633,286 A | 5/1997 | Chen |
| 5,683,349 A | 11/1997 | Makower et al. |
| 5,807,403 A | 9/1998 | Beyar et al. |
| 5,836,314 A | 11/1998 | Benderev et al. |
| 5,836,315 A | 11/1998 | Benderev et al. |
| 5,842,478 A | 12/1998 | Benderev et al. |
| 5,860,425 A | 1/1999 | Benderev et al. |
| 5,899,909 A | 5/1999 | Claren et al. |
| 5,934,283 A | 8/1999 | Willem et al. |
| 5,944,732 A | 8/1999 | Raulerson et al. |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,039,686 A * | 3/2000 | Kovac .................... 600/30 |
| 6,042,534 A * | 3/2000 | Gellman et al. .......... 600/30 |
| 6,042,536 A | 3/2000 | Tihon et al. |
| 6,050,937 A | 4/2000 | Benderev |
| 6,053,935 A | 4/2000 | Brenneman et al. |
| 6,068,591 A | 5/2000 | Bruckner et al. |
| 6,071,290 A | 6/2000 | Compton |
| 6,106,545 A | 8/2000 | Egan |
| 6,110,101 A | 8/2000 | Tihon et al. |
| 6,117,067 A | 9/2000 | Gil-Vernet |
| 6,168,611 B1 | 1/2001 | Rizvi |
| 6,273,852 B1 | 8/2001 | Lehe et al. |
| 6,302,840 B1 | 10/2001 | Benderev |
| 6,322,492 B1 * | 11/2001 | Kovac .................... 600/30 |
| 6,328,686 B1 * | 12/2001 | Kovac .................... 600/30 |
| 6,328,744 B1 | 12/2001 | Harari et al. |
| 6,334,446 B1 | 1/2002 | Beyar |
| 6,382,214 B1 | 5/2002 | Raz et al. |
| 6,406,423 B1 | 6/2002 | Scetbon |
| 6,406,480 B1 | 6/2002 | Beyar et al. |
| 6,423,080 B1 * | 7/2002 | Gellman et al. .......... 606/148 |
| 6,478,727 B2 | 11/2002 | Scetbon |
| 6,502,578 B2 | 1/2003 | Raz et al. |
| 2001/0049467 A1 | 12/2001 | Lehe et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0077526 A1 | 6/2002 | Kammerer et al. |
| 2002/0091373 A1 | 7/2002 | Berger |
| 2002/0099260 A1 | 7/2002 | Suslian et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |

FOREIGN PATENT DOCUMENTS

| | | |
|---|---|---|
| EP | 0 650 703 A1 | 6/1994 |
| EP | 0 643 945 A2 | 7/1994 |
| EP | 1 093 758 A1 | 4/2001 |
| SU | 1225547 A1 | 4/1986 |
| SU | 1342486 A | 10/1987 |
| WO | WO 93/17635 A1 | 9/1993 |
| WO | Wo 93/19678 A2 | 10/1993 |
| WO | WO 98/19606 A1 | 5/1998 |
| WO | WO 98/35616 A1 | 8/1998 |
| WO | WO 98/35632 A1 | 8/1998 |
| WO | WO 99/52450 A1 | 10/1999 |
| WO | WO 00/64370 A1 | 2/2000 |
| WO | WO 00/13601 A1 | 3/2000 |
| WO | WO 00/18319 A1 | 4/2000 |
| WO | WO 00/57812 A1 | 10/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/39670 A1 | 6/2001 |
| WO | WO 01/45589 A1 | 6/2001 |
| WO | WO 01/56499 A1 | 8/2001 |
| WO | WO 02/28312 A1 | 4/2002 |
| WO | WO 02/32284 A2 | 4/2002 |
| WO | WO 02/34124 A2 | 5/2002 |

OTHER PUBLICATIONS

Beck, Peter R. et al., Treatment of Urinary Stress Incontinence With Anterior Colporrhaphy, Obstetrics and Gynecology, vol 59 (No. 3), pp. 269–274 (Mar. 1982).

Benderev, Theodore V., MD, A Modified Percutaneous Outpatient Bladder Neck Suspension System, Journal of Urology, vol. 152, pp. 2316–2320 (Dec. 1994).

Benderev, Theodore V., MD, Anchor Fixation and Other Modifications of Endoscopic Bladder Neck Suspension, Urology, vol 40, No. 5, pp. 409–418 (Nov. 1992).

Bergman, Arieh et al., Three Surgical Procedures for Genuine Stress Incontinence: Five–Year Follow–Up of a Prospective Randomized Study, Am J Obstet Gynecol, vol 173 No 1, pp. 66–71 (Jul. 1995).

Blaivas, Jerry et al., Pubovaginal Fascial Sling for the Treatment of Complicated Stress Urinary Incontinence, The Journal of Urology, vol. 145, pp. 1214–1218 (Jun. 1991).

Blaivas, Jerry et al., Type III Stress Urinary Incontinence: Importance of Proper Diagnosis and Treatment, Surgical Forum, pp. 473–475, (1984).

Blaivas, Jerry, Commentary Pubovaginal Sling Procedure, Surgery for Female Urinary Incontinence, Current Operative Urology, pp. 93–101 (1990).

Blavis, Jerry, Commentary: Pubovaginal Sling Procedure, Experience with Pubovaginal Slings, pp. 93–101.

Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292–294 (Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281–290 (1961).

Choe, Jong M. et al., Gore–Tex Patch Sling: 7 Years Later, Urology, vol. 54, pp. 641–646 (1999).

Cook/Ob Gyn®, Urogynecology, Copyright Cook Urological Inc., pp. 1–36 (1996).

Das, Sakti et al., Laparoscopic Colpo–Suspension, The Journal of Urology, vol. 154, pp. 1119–1121 (Sep. 1995).

Decter, Ross M., Use of the Fascial Sling for Neurogenic Incontinence: Lessons Learned, The Journal of Urology, vol. 150, pp. 683–686 (Aug. 1993).

DeLancey, John, MD, Structural Support of the Urethra as it Relates to Stress Urinary Incontinence: The Hammock Hypothesis, Am J Obstet Gynecol, vol 170, No 6, pp. 1713–1723 (Jun. 1994).

Enzelsberger, H. et al., Urodynamic and Radiologic Parameters Before and After Loop Surgery for Recurrent Urinary Stress Incontinence, Acta Obstet Gynecol Scand, 69, pp. 51–54 (1990).

Eriksen, Bjarne C. et al., Long–Term Effectiveness of the Burch Colposuspension in Female Urinary Stress Incontinence, Acta Obstet Gynecol Scand, 69, pp. 45–50 (1990).

Falconer, C. et al., Clinical Outcome and Changes in Connective Tissue Metabolism After Intravaginal Slingplasty in Stress Incontinence Women, International Urogynecology Journal, pp. 133–137 (1966).

Falconer, C. et al., Influence of Different Sling Materials of Connective Tissue Metabolism in Stress Urinary Incontinent Women, International Urogynecology Journal, Supp. 2, pp. S19–S23 (2001).

Gilja, Ivan et al., A Modified Raz Bladder Neck Suspension Operation (Transvaginal Burch), The Journal of Urology, vol. 153, pp. 1455–1457 (May 1995).

Gittes, Ruben F. et al., No–Incision Pubovaginal Suspension for Stress Incontinence, The Journal of Urology, vol. 138 (Sep. 1987).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol 131, No 1, pp. 77–82 (Mar. 1, 1978).

Hodgkinson, C. Paul et. al., Urinary Stress Incontinence in the Female, Department of Gynecology and Obstetrics, Henry Ford Hospital, vol 10, No. 5, p. 493–499, (Nov. 1957).

Holschneider, C. H., et al., The Modified Pereyra Procedure in Recurrent Stress Urinary Incontinence: A 15–year Review, Obstetrics & Gynecology, vol. 83, No. 4, pp. 573–578 (Apr. 1994).

Horbach, Nicollette S., et al., Instruments and Methods, A Suburethral Sling Procedure with Polytetrafluoreothylene for the Treatment of Genuine Stress Incontinence in Patients with Low Urethral Closure Pressure, Obstetrics & Gynecology, vol. 71, No. 4, pp. 648–652 (Apr. 1998).

Ingelman–Sunberg, A. et al., Surgical Treatment of Female Urinary Stress Incontinence, Contr. Gynec. Obstet., vol. 10, pp. 51–69 (1983).

IVS Tunneller, AMA, (no date) 4 pages.

Jeffcoate, T.N.A. et al., The Results of the Aldridge Sling Operation for Stress Incontinence, Journal of Obstetrics and Gynaecology, pp. 36–39 (1956).

Karram, Mickey et al., Patch Procedure: Modified Transvaginal Fascia Lata Sling for Recurrent for Severe Stress Urinary Incontinence, vol. 75, pp. 461–463 (Mar. 1990).

Kersey, J., The Gauze Hammock Sling Operation in the Treatment of Stress Incontintence, British Journal of Obstetrics and Gynaecology, vol. 90, pp. 945–949 (Oct. 1983).

Klutke, Carl et al., The Anatomy of Stress Incontinence: Magnetic Resonance Imaging of the Female Bladder Neck and Urethra, The Journal of Urology, vol 143, pp. 563–566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294–296 (Aug. 1996).

Klutke, John M.D. et al, The promise of tension–free vaginal tape for female SUI, Contemporary Urology, 7 pages (Oct. 2000).

Korda, A. et al., Experience With Silastic Slings for Female Urinary Incontience, Aust NZ J. Obstet Gynaecol, vol. 29, pp. 150–154 (May 1989).

Kovac, S. Robert, et al, Pubic Bone Suburethral Stabilization Sling for Recurrent Urinary Incontinence, Obstetrics & Gynecology, vol. 89, No. 4, pp. 624–627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow–up of the Pubic Bone Suburethral Stabilization Sling Operation for Recurrent Urinary Incontinence (Kovac Procedure), Journal of Pelvic Surgery, pp. 156–160 (May 1999).

Kovac, Stephen Robert, M.D., Cirriculum Vitae, pp. 1–33 (Jun. 18, 1999).

Leach, Gary E., et al., Female Stress Urinary Incontinence Clinical Guidelines Panel Report on Surgical Management of Female Stress Urinary Incontinence, American Urological Association, vol. 158, pp. 875–880 (Sep. 1997).

Leach, Gary E., MD, Bone Fixation Technique for Transvaginal Needle Suspension, Urology vol XXXI, No. 5, pp. 388–390 (May 1988).

Lichtenstein, Irving L. et al, The Tension Free Herinoplasty, The American Journal of Surgery, vol. 157, pp 188–193 (Feb. 1989).

Loughlin, Kevin R. et al., Review of an 8–Year Experience With Modifications of Endoscopic Suspension of the Bladder Neck for Female Stress Incontinence, The Journal of Uroloyg, vol. 143, pp. 44–45 (1990).

Marshall, Victor Fray et al. The Correction of Stress Incontinence by Simple Vesicourethral Suspension, Surgery, Gynecology and Obstetrics, vol. 88, pp. 509–518 (1949).

Marshall, Victor Fray et al., The Correction of Stress Incontinence by Simple Vesicourethral Suspension, Surgery, Gynecology and Obstetrics, vol. 88, pp. 509–518 (May 1949).

McGuire, Edward J. et al., Pubovaginal Sling Procedure for Stress Incontinence, The Journal of Urology, vol. 119, pp. 82–84 (Jan. 1978).

McGuire, Edward J. et al., Abdominal Procedures for Stress Incontinence, Urologic Clinics of North America, pp. 285–290, vol. 12, No. 2 (May 1985).

McGuire, Edward J. et al., Experience With Pubovaginal Slings for Urinary Incontinence at the University of Michigan, Journal of Urology, vol. 138, pp. 90–93(1987).

McGuire, Edward J., M.D., The Sling Procedure for Urinary Stress Incontinence, Profiles in Urology, pp. 3–18.

McGuire, Edwared J. et al., Abdominal Fascial Slings, Slings, Raz Female Urology, p 369–375 (1996).

McIndoe, G. A. et al., The Aldridge Sling Procedure in the Treatment of Urinary Stress Incontinence, Aust. N Z Journal of Obstet Gynecology, pp. 238–239 (Aug. 1987).

McKiel, Charles F. Jr., et al, Marshall–Marchetti Procedure Modification, vol 96, pp. 737–739 (Nov. 1966).

Mitek Brochure, Therapy of Urinary Stess Incontinence in Women Using Mitek GIII Anchors, By Valenzio C. Mascio, MD.

Moir, J. Chassar et. al., The Gauze–Hammock Operation, The Journal of Obstetrics and Gynaecology of British Commonwealth, vol. 75 No. 1, pp. 1–9 (Jan. 1968).

Morgan, J. E., A Sling Operation, Using Marlex Polypropylene Mesh, for the Treatment of Recurrent Stress Incontinence, Am. J. Obst. & Gynecol, pp. 369–377 (Feb. 1970).

Morgan, J. E. et al., The Marlex Sling Operation for the Treatment of Recurrent Stress Urinary Incontinence: A 16–Year Review, American Obstetrics Gynecology, vol. 151, No. 2, pp. 224–226 (Jan. 1998).

Narik, G. et.al., A Simplified Sling Operation Suitable for Routine Use, Gynecological and Obstetrical Clinic, University of Vienna, vol. 84, No 3, p. 400–405, (Aug. 1, 1962).

Nichols, David H., The Mersilene Mesh Gauze–Hammock for Severe Urinary Stress Incontinence, Obstetrics and Gynecology, vol. 41, pp. 88–93 (Jan. 1973).

Norris, Jeffrey P. et al., Use of Synthetic Material in Sling Surgery: A Minimally Invasive Approach, Journal of Endourology, vol. 10, pp. 227–230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389–392 (Jan. 1992).

Ostergard, Donald R. et al., Urogynecology and Urodynamics Theory and Practice, pp. 569–579 (1996).

Parra, R. O., et al, Experience With a Simplified Technique for the Treatment of Female Stress Urinary Incontinence, British Journal of Urology, pp. 615–617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45–50 (1999).

Pereyra, Armand J. et al, Pubourethral Supports in Perspective: Modified Pereyra Procedure for Urinary Incontinence, Obstetrics and Gynecology, vol. 59, No. 5, pp 643–648 (May 1982).

Pereyra, Armand J., M.D., F.A.C.S., A Simplified Procedure for Correction of Stress Incontinence in Women, West.J. Surg., Obst. & Gynec, p. 223–226, (Jul.–Aug. 1959).

Peter E. Papa Petros et al., Cure of Stress Incontinence by Repair of External Anal Sphincter, Acta Obstet Gynecol Scand, vol 69, Sup 153, p. 75 (1990).

Peter Petros et al., Anchoring the Midurethra Restores Bladder–Neck Anatomy and Continence, The Lancet, vol 354, pp. 997–998 (Sep. 18, 1999).

Petros, Peter E. Papa et al., An Anatomical Basis for Success and Failure of Female Incontinence Surgery, Scandinavian Journal of Neurourology and Urodynamics, Sup 153, pp. 55–60 (1993).

Petros, Peter E. Papa et al., An Analysis of Rapid Pad Testing and the History for the Diagnosis of Stress Incontinence, Acta Obstet Gynecol Scand, vol 71, pp. 529–536 (1992).

Petros, Peter E. Papa et al., An Integral Theory of Female Urinary Incontinence, Acta Obstetricia et Gynecologica Scandinavica, vol. 69 Sup. 153, pp. 7–31 (1990).

Petros, Peter E. Papa et al., Bladder Instability in Women: A Premature Activation of the Micturition Reflex, Scandinavian Journal of Neurourology and Urodynamics, Sup 153, pp. 235–239 (1993).

Petros, Peter E. Papa et al., Cough Transmission Ratio: An Indicator of Suburethral Vaginal Wall Tension Rather Than Urethral Closure?, Acta Obstet Gynecol Scand, vol. 69, Sup 153, pp. 37–39 (1990).

Petros, Peter E. Papa et al., Cure of Urge Incontinence by the Combined Intravaginal Sling and Tuck Operation, Acta Obstet Gynecol Scand, vol 69, Sup 153, pp. 61–62 (1990).

Petros, Peter E. Papa et al., Further Development of the Intravaginal Slingplasty Procedure—IVS III—(With Midline "Tuck"), Scandinavian Journal of Neurourology and Urodynamics, Sup 153, pp. 69–71 (1993).

Petros, Peter E. Papa et al., Medium–Term Follow–Up of the Intravaginal Slingplasty Operation Indicates Minimal Deterioration of Urinary Continence With Time, (3 pages) (1999).

Petros, Peter E. Papa et al., Non Stress Non Urge Female Urinary Incontinence—Diagnosis and Cure: A Preliminary Report, Acta Obstet Gynecol Scand, vol 69, Sup 153, pp. 69–70 (1990).

Petros, Peter E. Papa et al., Part I: Theoretical, Morphological, Radiographical Correlations and Clinical Perspective, Scandinavian Journal of Neuourology and Urodynamics, Sup 153, pp. 5–28 (1993).

Petros, Peter E. Papa et al., Part II: The Biomechanics of Vaginal Tissue and Supporting Ligaments With Special Relevance to the Pathogenesis of Female Urinary Incontinence, Scandinavian Journal of Neurourolgy and Urodynamics, Sup 153, pp. 29–40 plus cover sheet (1993).

Petros, Peter E. Papa et al., Part III: Surgical Principles Deriving From the Theory, Scandinavian Journal of Neurourology and Urodynamics, Sup 153, pp. 41–52 (1993).

Petros, Peter E. Papa et. al., Part IV: Surgical Appliations of the Theory—Development of the Intravaginal Sling Pklasty (IVS) Procedure, Scandinavian Journal of Neurourology and Urodynamics, Sup 153, pp. 53–54 (1993).

Petros, Peter E. Papa et al., Pelvic Floor Rehabilitation According to the Integrated Theory of Female Urinary Incontinence, Chapter 7, pp. 249–258 (book chapter).

Petros, Peter E. Papa et al., Pinch Test for Diagnosis of Stress Urinary Incontinence, Acta Obstet Gynecol Scand, vol. 69, Sup 153, pp. 33–35 (1990).

Petros, Peter E. Papa et al., Pregnancy Effects on the Intravaginal Sling Operation, Acta Obstet Gynecol Scand, vol 69, Sup 153, pp. 77–79 (1990).

Petros, Peter E. Papa et al., The Autogenic Ligament Procedure: A Technique for Planned Formation of an Artificial Neo–Ligament, Acta Obstet Gynecol Scand, vol 69, Sup 153, pp. 43–51 (1990).

Petros, Peter E. Papa et al., The Combined Intravaginal Sling and Tuck Operation an Ambulatory Procedure for Cure of Stress and Urge Incontinence, Acta Obstet Gynecol Scand, vol 69, Sup 153, pp. 53–59 (1990).

Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61–67 (1993).

Petros, Peter E. Papa et al., The Free Graft Procedure for Cure of the Tethered Vagina Syndrome, Scandinavian Journal of Neurourology and Urodynamics, Sup 153, pp. 85–87 (1993).

Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, pp. 73–75 (1993).

Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77–79 (1993).

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81–84 (1993).

Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89–93 (1993).

Petros, Peter E. Papa et al., The Role of a Lax Posterior Vaginal Fornix in the Causation of Stress and Urgency Symptoms: A Preliminary Report, Acta Obstet Gynecol Scand, vol 69, Sup 153, pp. 71–73 (1990).

Petros, Peter E. Papa et al., The Tethered Vagina Syndrome, Post Surgical Incontinence and I–Plasty Operation for Cure, Acta Obstet Gynecol Scand, vol 69, Sup 153, pp. 63–67 (1990).

Petros, Peter E. Papa et al., The Tuck Procedure: A Simplified Vaginal Repair for Treatment of Female Urinary Incontinence, Acta Obstet Gynecol Scand, vol 69, Sup 153, pp. 41–42 (1990).

Petros, Peter E. Papa et al., Urethral Pressure Increase on Effort Originates From Within the Urethra, and Continence from Musculovaginal Closure, Scandinavian Journal of Neurourology and Urodynamics, pp. 337–350 (1995).

Petros, Peter E. Papa, Development of Generic Models for Ambulatory Vaginal Surgery—Preliminary Report, International Urogynecology Journal, pp. 20–27 (1998).

Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270–278, (1997).

Rackley, Raymond R. et al., Tension–Free Vaginal Tape and Percutaneous Vaginal Tape Sling Procedures, Techniques in Urology, vol. 7, No. 2, pp. 90–100 (2001).

Rackley, Raymond R. M.D., Synthetic Slings: Five Steps for Successful Placement, Urology Times, p. 46, 48, 49 (Jun. 2000).

Raz, Shlomo, et al., The Raz Bladder Neck Suspension Results in 206 Patients, The Journal of Urology, pp. 845–846 (1992).

Raz, Shlomo, Female Urology, pp. 80–86, 369–398, 435–442 (1996).

Raz, Shlomo, MD, Modified Bladder Neck Suspension for Female Stress Incontinence, Urology, vol. XVII, No. 1, pp. 82–85 (Jan. 1981).

Richardson, David A. et al., Delayed Reaction to the Dacron Buttress Used in Urethropexy, The Journal of Reproductive Medicine, pp. 689–692, vol. 29, No. 9 (Sep. 1984).

Ridley, John H., Appraisal of the Goebell–Frangeheim–Stoeckel Sling Procedure, American Journal Obst & Gynec., vol. 95, No. 5, pp 741–721 (Jul. 1, 1986).

Roberts, Henry, M.D., Cystourethrography in Women, Deptment of Obstetrics and Gynaecology, University of Liverpool, May 1952, vol. XXXV, No. 293, pp. 253–259.

Sloan W. R. et al., Stress Incontinence of Urine: A Retrospective Study of the Complications and Late Results of Simple Suprapubic Suburethral Fascial Slings, The Journal of Urology, vol. 110, pp. 533–536 (Nov. 1973).

Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411–415 (Mar. 1987).

Stamey, Thomas A., M.D., Endoscopic Suspension of the Vesical Neck for Urinary Incontinence in Females, Ann. Surgery, vol. 192 No. 4, pp. 465–471 (Oct. 1980).

Stanton, Stuart L., Suprapubic Approaches for Stress Incontinence in Women, Journal of American Geriatrics Society, vol. 38, No. 3, pp. 348–351 (Mar. 1990).

Stanton, Stuart, Springer–Veglag, Surgery of Female Incontinence, pp. 105–113 (1986).

Staskin et al., A Comparison of Tensile Strength Among Three Preparations of irradiated and Non–Irradiated Human Fascia Lata Allografts, 2 pages (1992).

Staskin, David R. et al., The Gore–Tex Sling Procedure for Female Sphincteric Incontinence: Indications, Technique, and Results, World Journal of Urology, vol. 15, pp. 295–299 (1997).

Studdiford, William E., Transplantation of Abdominal Fascia for the Relief of Urinary Stress Incontinence, American Journal of Obstetrics and Gynecology, pp. 764–775 (1944).

Suport™, Sub–Urethral Perineal Retro–Pubic Tensionless Sling, Matrix Medical (Pty) Ltd, (no date), 1 pg.

TVT Tension–free Vaginal Tape, Gynecare, Ethicon, Inc., 23 pages (1999).

Ulmsten, U. et al., A Multicenter Study of Tension–Free Vaginal Tape (TVT) for Surgical Treatment of Stress Urinary Incontinence, International Urogynecology Journal, vol 9, pp. 210–213 (1998).

Ulmsten, U. et al., An Ambulatory Surgical Procedure Under Local Anesthesia for Treatment of Female Urinary Incontinence, International Urogynecology Journal, vol. 7, pp 81–86 (May 1996).

Ulmsten, U., Female Urinary Incontinence—A Symptom, not a Urodynamic Disease. Some Theoretical and Practical Aspects on the Diagnosis a Treatment of Female Urinary Incontinence, International Urogynecology Journal, vol 6, pp. 2–3 (1995).

Ulmsten, Ulf et al., A Three Year Follow Up of Tension Free Vaginal Tape for Surgical Treatment of Female Stress Urinary Incontinence, British Journal of Obstetrics and Gynaecology, vol 106, pp. 345–350 (1999).

Ulmsten, Ulf et al., Different Biochemical Composition of Connective Tissue in Continent, Acta Obstet Gynecol Scand, pp. 455–457 (1987).

Ulmsten, Ulf et al., Intravaginal Slingplasty (IVS): An Ambulatory Surgical Procedure for Treatment of Female Urinary Incontinence, Scand J Urol Nephrol, vol 29, pp. 75–82 (1995).

Ulmsten, Ulf et al., The Unstable Female Urethra, Am. J. Obstet. Gynecol., vol. 144 No. 1, pp. 93–97 (Sep. 1, 1982).

Vesica® Sling Kits, Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93–100, vol 21 (Mar. 1996).

Webster, George D., Female Urinary Incontinence, Urologic Surgery, pp. 665–679.

Webster, George et al., Voiding Dysfunction Following Cystourethropexy: Its Evaluation and Management, The Journal of Urology, vol. 144, pp. 670–673 (Sep. 1990).

Winter, Chester C., Peripubic Urethropexy for Urinary Stress Incontinence in Women, Urology, vol. XX, No. 4, pp. 408–411 (Oct. 1982).

Woodside, Jeffrey R. et al., Suprapubic Endoscopic Vesical Neck Suspension for the Management of Urinary Incontinence in Myelodysplastic Girls, The Journal of Urology, vol. 135, pp. 97–99 (Jan. 1986).

Zacharin, Robert et al., Pulsion Enterocele: Long–Term Results of an Abdominoperineal Technique, Obstetrics & Gynecology, vol. 55 No. 2, pp. 141–148 (Feb. 1980).

Zacharin, Robert, The Suspensory Mechanism of the Female Urethra, Journal of Anatomy, vol. 97, Part 3, pp. 423–427 (1963).

Zimmern, Phillippe E. et al., Four–Corner Bladder Neck Suspension, Vaginal Surgery for the Urologist, vol 2, No. 1, pp. 29–36 (Apr. 1994).

* cited by examiner

SLING SYSTEM FOR TREATING INCONTINENCE

REFERENCE TO RELATED APPLICATION

This application is a Continuation of patent application Ser. No. 9/236,210, filed Jan. 23, 1999 now U.S. Pat. No. 6,322,492; which is a Continuation of patent application Ser. No. 09/111,525 filed Jul. 8, 1998 now U.S. Pat. No. 6,039,686; which is a Continuation-in-part of patent application Ser. No. 08/820,053 filed Mar. 18, 1997, now abandoned; all of which are incorporated herein by reference.

TECHNICAL FIELD

The invention relates to a system and method for the effective long-term cure of recurrent female urinary incontinence, and more particularly to a urethra stabilization and support system attached to the posterior/inferior pubic bone and a method for accomplishing this in which the urethra is positioned in the anatomically proper position.

BACKGROUND ART

The problem of recurrent female urinary incontinence, or the inability to control urination, is a major and debilitating one affecting millions of women in the United States alone. One particular type that frequently occurs in women is stress urinary incontinence, which is precipitated by coughing, straining, or heavy lifting. Mild cases may be treated by exercises involving tightening and relaxing of the perineal and gluteal muscles or by sympathomimetic drug therapy. Severe cases, however, may require surgery to correct the underlying anatomic defect. It is this surgical correction which is the subject of the present invention.

In general, continence is considered to be a function of urethral support and coaptation. For coaptation to successfully prevent or cure incontinence, the urethra must be supported and stabilized in its normal anatomic position. The female's natural support system for the urethra is a hammock-like supportive layer composed of endopelvic fascia, the anterior vaginal wall, and a distal attachment to the pubic bone. Weakening and elongation of the pubourethral ligaments and the arcus tendineus fascia pelvis, weakening of the endopelvic fascia and pubourethral prolapse of the anterior vaginal wall, and their complex interaction with intraabdominal forces are all suspected to play a role in the loss of pelvic support for the urethra and subsequent hypermobility to an unnaturally low non-anatomic position, leading to urinary incontinence.

Many procedures have been devised to treat urinary incontinence with the goal of elevating the neck of the bladder to return it to a higher retropubic position. Some involve the creation of a compensatory pubovaginal sling through a variety of needle suspension procedures; others employ a suburethral mesh to act as a compensatory suburethral sling to avoid the possibility that the sutures used in the needles suspension procedures will easily tear.

Many of the needle suspension procedures involve placing sutures in the endopelvic fascia or the anterior vaginal wall on either side of the urethra and attaching them to fixation sites such as bone and soft tissue. Alternatively, the sutures are attached to artificial anchors placed within the pelvis, at the superior border of the pubis, or rectus abdominus fascia. A major problem with this type of procedure is that the very fascial and muscular support structures that are sutured for support are often stretched, damaged, or otherwise deficient to begin with, and remain so after the procedure. It is therefore difficult to employ them successfully as reinforcements for surgical repair.

The pubovaginal sling procedure, in which a mesh is placed under the urethra to provide elevation and support of the urethra and bladder neck, has enjoyed an excellent surgical success rate. It is generally preferable for more complicated cases of recurrent genuine stress urinary incontinence, particularly in patients who have failed prior surgery, who are obese, or whose lifestyles involve heavy lifting and accompanying increased intraabdominal pressure. However, problems with voiding disfunction and urinary retention, detrusor instability, and infection and erosion of sling materials that can lead to urethrovesical and vesicovaginal fistulas are cause for concern. Additionally, this procedure is more technically challenging, presents greater blood loss, longer operative time, and a prolonged postoperative recovery.

These techniques use a variety of attachment sites for bladder neck and urethral support, such as the superior portion of the pubis, Cooper's ligament, or rectus abdominus fascia. This results in placement of the urethra in an unnaturally high position with respect to its normal anatomical retropubic position so that problems with voiding and urinary retention frequently arise after the procedure. Further, this abnormal positioning of the urethra in conjunction with failure of the supporting tissues and poor surgical technique have often led to a recurrence of incontinence since all of these operations create a compensatory abnormality rather than restoring the normal anatomy.

A related difficulty that contributes to the unnatural positioning of the urethra is that some attachment sites, such as the rectus abdominus fascia, require very long sutures and accompanying difficulty in achieving the proper tension in the sutures. This can result in increased lateral movement and momentum of the support structures or mesh sling when they are moved due to intraabdominal pressures.

The present invention addresses and corrects these and other difficulties by affecting the continence mechanism directly and providing a predictable and lasting permanent cure for the problem of recurrent female urinary incontinence.

It has been found that the key site for control of continence has not been heretofore addressed. It has further been found that the urethral hypermobility observed in most incontinent patients is caused by a lax or torn arcus tendineus facia pelvis attachment at its origin near the anterior levator arch in the immediate retropubic position at the site of the pubourethral ligaments. Repair and reinforcement of this area to stabilize the urethra in its normal position may be equally important as repair of the endopelvic facia. Therefore, the key site for control of continence is the paraurethral attachments of the pubourethral ligaments to the sides of the urethra at the intermediate 60% of the urethral length. This is simulated through the employment of a mesh sling system which supports this site and restores the bladder neck and urethra to their normal anatomic retropubic position. Additionally, when placed in this position, the lateral sides of the mesh serve to act as pubourethral ligaments which help to prevent undue descent of the urethra.

It has also been found that although the superior portion of the pubic bone is a functional and secure fixation site for incontinence repair, a key to restoring the urethra to its normal anatomical position is using the posterior/inferior border of the pubic bone, not the superior portion, as the attachment sites for the mesh sling system. Proper tensioning of the mesh sling system is made easier by using this portion of the pubic bone as the attachment site, due in part to the fact that shorter sutures and an innovative mesh suturing pattern is used. This serves to avoid the problems heretofore discussed associated with an improperly high retropubic positioning of the urethra.

DISCLOSURE OF THE INVENTION

According to the invention there is provided a pubic bone-mounted urethra stabilization and support system and a method for the long term cure of recurrent female urinary incontinence.

The system comprises a pair of anchors affixed to the posterior/inferior pubic bone, sutures attached to the anchors, and a mesh sling passing behind and about the urethra and the adjacent endopelvic fascia and having ends attached to the anchors by the anchor-mounted sutures. In particular, a pair of anchor screws are located on either side of the symphysis pubis in the retropubic area posteriorly and at about 0.5 cm superiorly of the inferior edge of the ischial ramus. Sutures connect the anchor screws to the mesh sling. The mesh sling directly supports the urethra by its placement on the endopelvic fascia in the area of the intermediate 60 percent portion of the urethra as will be later described in greater detail.

The method includes the steps of accessing said urethra and pubic bone, properly locating and attaching the anchors to the pubic bone, properly locating the sling about the urethra and suturing and tensioning the ends of the sling to the anchors, causing said sling to restore, support and stabilize functional urethral continence anatomy and prevent urethral descent under intraabdominal pressure.

To access the urethra and pubic bone, a pair of divergent incisions are made, beginning at the posterior urethral fold, in the anterior vaginal wall. This creates a triangular flap to expose the operative field. Care must be taken to separate the anterior vaginal wall from the adjoining endopelvic fascia to leave the endopelvic fascia intact. Direct visualization and palpation is next employed to evaluate the integrity of the lateral attachment of the endopelvic fascia to each arcus tendineus fascia pelvis, repairing any damage by suturing if necessary.

The pubic bone is next located by palpation. The course of the arcus from the ischial spine to the arcus insertion into the posterior/inferior aspect of the pubic bone is palpated to locate the proper site for the anchor screws, which is at either side of the symphysis pubis in the retropubic area posteriorly and at about 0.5 cm superiorly of the inferior edge of the ischial ramus. An anchor screw, which is provided with a pair of permanent sutures, is driven into the pubic bone at this location and set. An identical anchor screw is then driven into a symmetrically located position on the other side of the symphysis pubis.

A sling, comprised of a substantially rectangular patch of surgical mesh, is next laid upon the endopelvic fascia such that its longitudinal edges extend transversely of the urethra which is below the endopelvic fascia. Four permanent sutures are used to transfix the mesh along the lateral borders of the urethra at the edges of the mesh. These sutures are so positioned as to create a slight trough-like space between the mesh and the endopelvic fascia and urethra. This space prevents undue tension on the urethra by the mesh when the mesh is formed into a sling. The permanent sutures of the anchor screws are then woven transversely of the mesh in opposite directions between the longitudinal edges of the mesh and inset from the transverse mesh edges. These sutures are then bilaterally tied with appropriate tensioning to transform the mesh into a sling.

Finally, any additional necessary repairs, including the sequential tying of the repair sutures for attaching the endopelvic fascia to the arcus tendineus fascia pelvis, are made. The cut edges of the anterior vaginal wall are approximated with sutures, and the cul-de-sac and posterior vaginal segment defects are repaired.

DETAILED DESCRIPTION OF THE INVENTION

Figure 1:
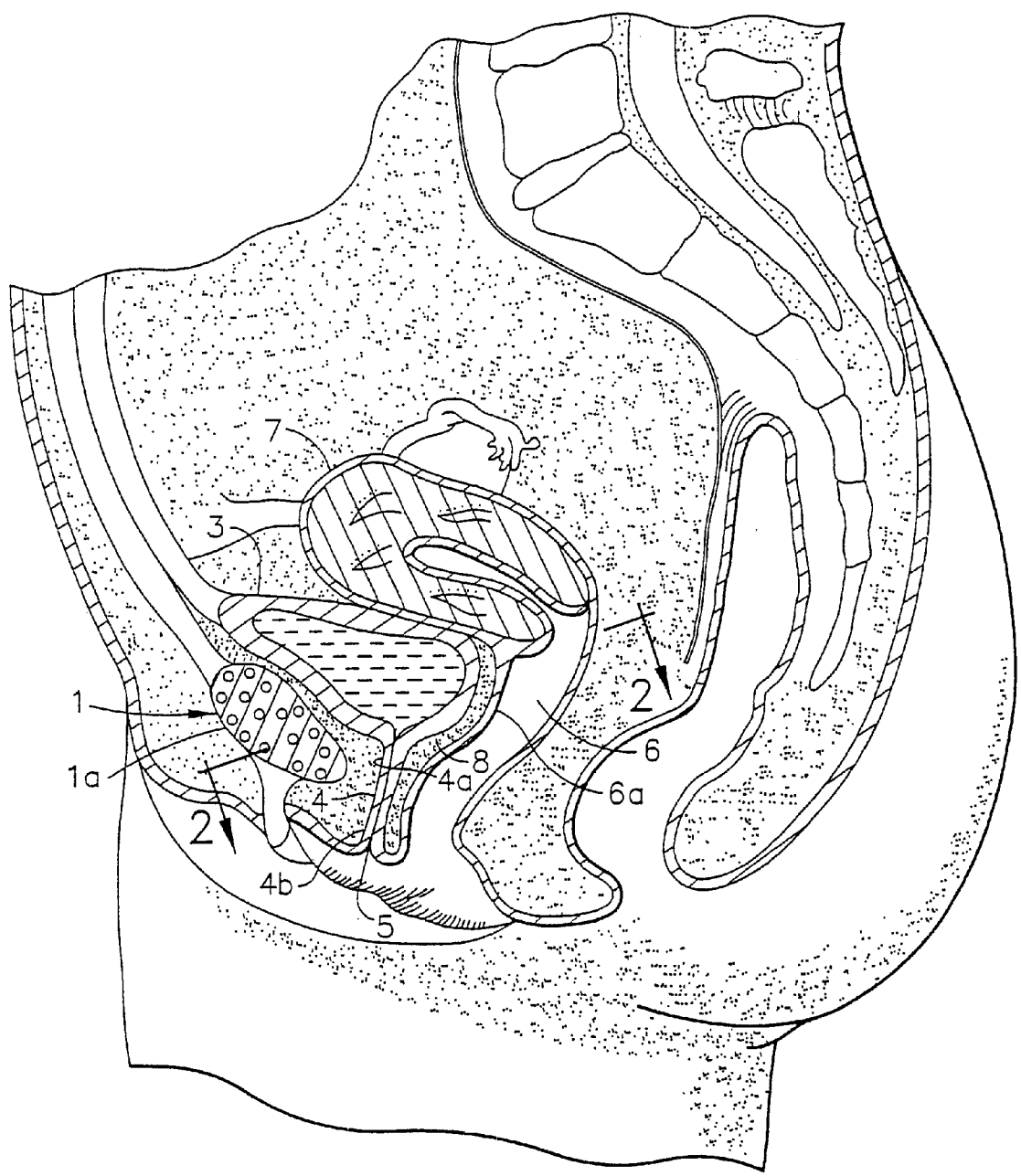
FIG. 1 is a fragmentary midsagittal cross-sectional view of the pelvic region illustrating the disposition of the urethra, bladder and vagina together with neighboring organs in a healthy woman.
Figure 2:
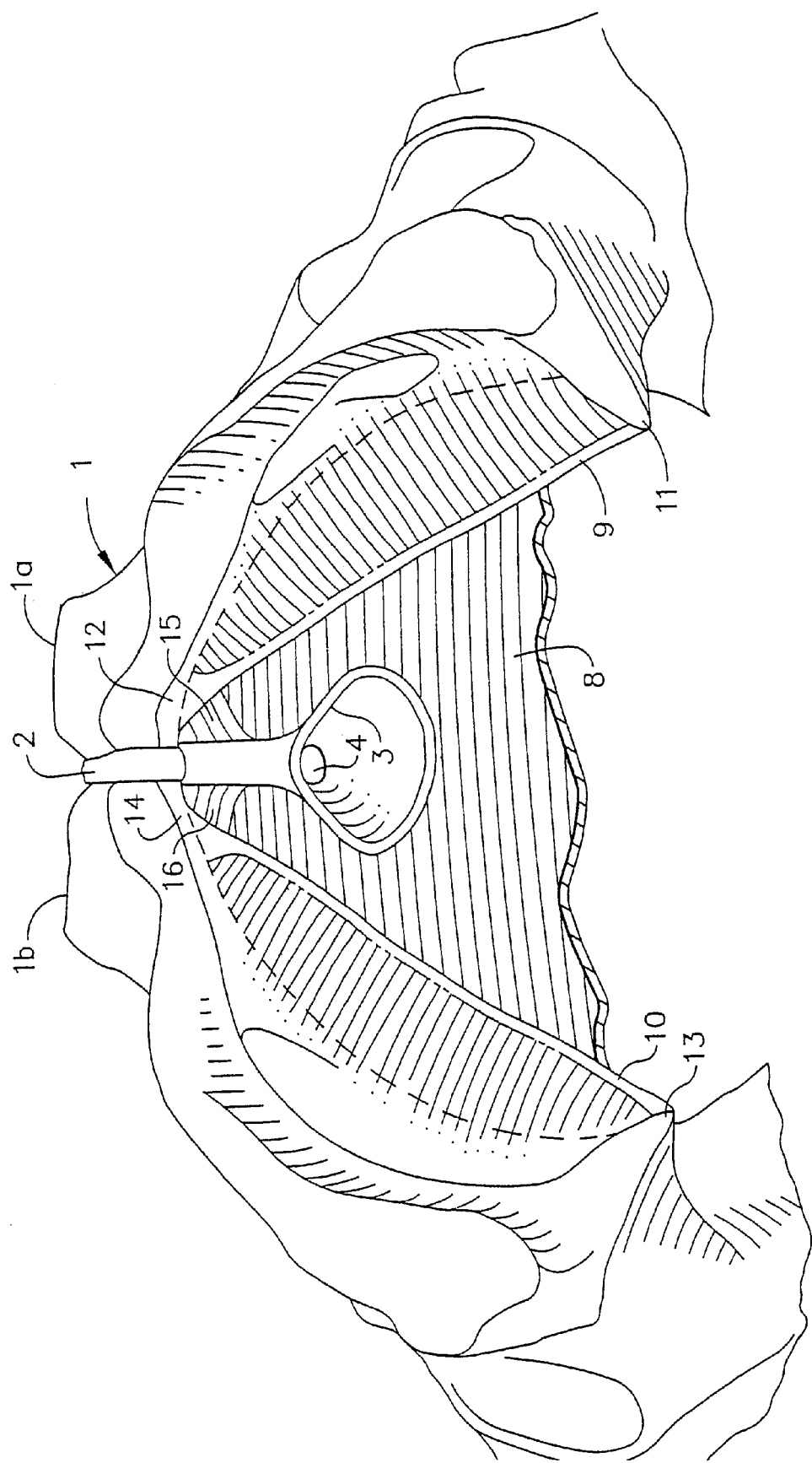
FIG. 2 is a fragmentary transverse view generally as seen along the line 2—2 of FIG. 1, illustrating the pubic bone, the bladder, the urethra, the arcus tendineus fascia, the endopelvic fascia and the pubourethral ligaments.
Figure 3:
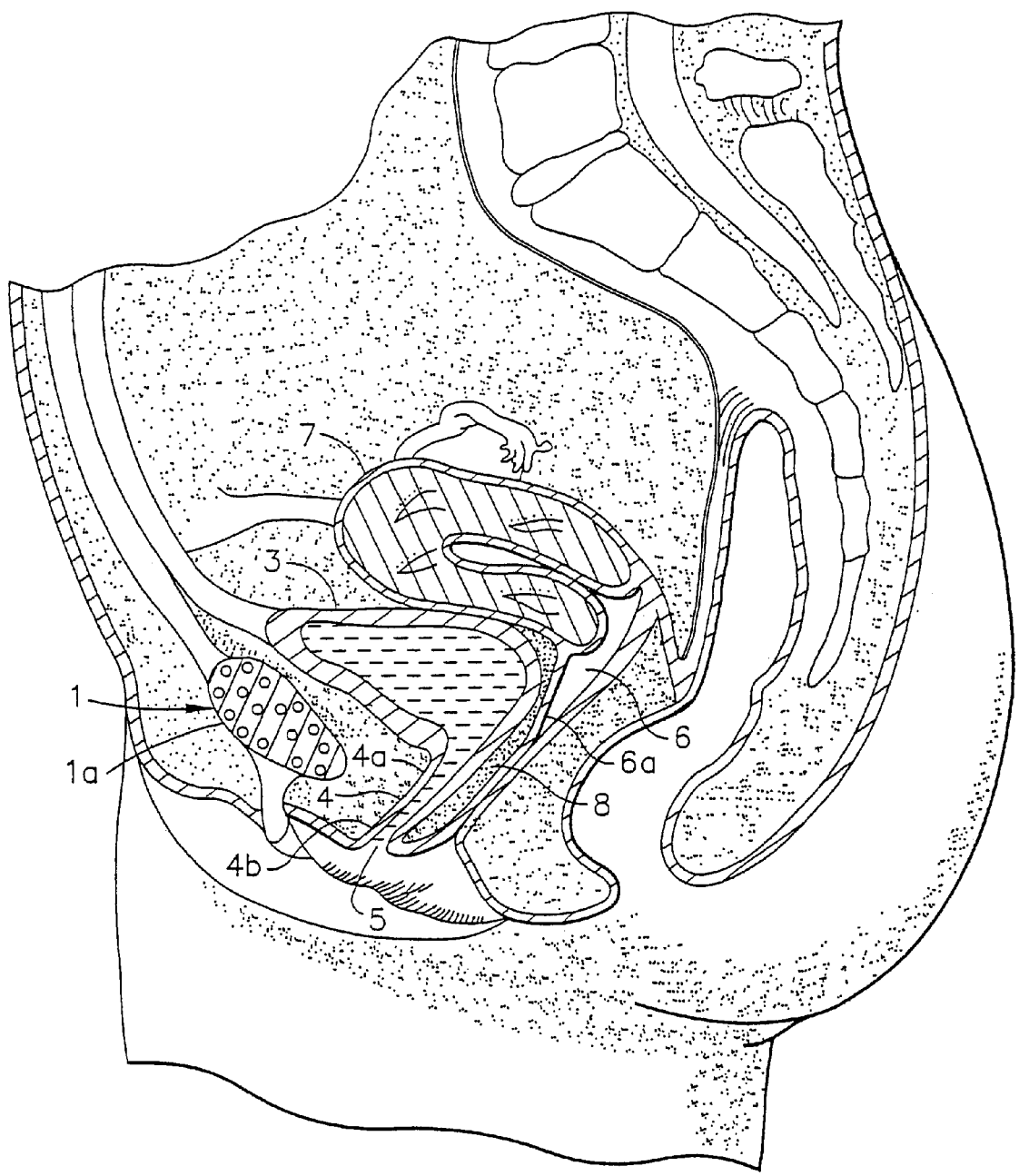
FIG. 3 is a fragmentary midsagittal cross-sectional view, similar to FIG. 1, and illustrating the prolapse of the urethra against the anterior wall of the vagina.

Throughout the drawings, like parts have been given like index numerals. Reference is first made to FIGS. 1 and 2.

These figures illustrate the location of the urethra and bladder of a healthy, continent female.

The pelvis is generally indicated at 1 in FIGS. 1 and 2. The forward bony portions of the pelvis 1a and 1b (i.e. the pubic bone) are joined together by the pubic symphysis 2. The bladder 3 is located above and behind the pubic bone 1a and 1b. The urethra extends from the bladder 3 downwardly to the urinary meatus 5.

The vagina 6 is located behind the bladder and urethra and is surmounted by the uterus 7 which overlies the bladder.

The upper 20 percent of the urethra constitutes the urethra-vesical junction or bladder neck portion. The lowermost 20 percent of the urethra leads to the urinary meatus 5. The intermediate 60 percent of the urethra (shown between index numerals 4a and 4b), is provided with a sphincteric mechanism, and support of this part of the urethra is believed to be of key importance for continence. This is the part of the urethra which is subject to the greatest pressure as the result of prolapse.

Attention is again directed to FIG. 1, and particularly to FIG. 2. It has long been understood that female continence is largely a factor of the proper support and stabilization of the bladder 3 and urethra 4 in their normal retropubic state and particularly during coughing, straining and the like. In the healthy, continent female, the urethra and bladder are separated from the extraabdominal area by a hammock-like supportive layer comprising the web of endopelvic fascia 8 and the anterior vaginal wall 6a. As is most clearly shown in FIG. 2, the web of endopelvic fascia 8 is attached to the arcus tendineus fascia pelvis 9 at the right side of the pelvis (as viewed in FIG. 2) and to the arcus tendineus fascia pelvis 10 on the left side of the pelvis (as viewed in FIG. 2). The arcus tendineus fascia pelvis 9 extends from the ischial spine 11 to its insertion in the pubic bone portion 1a at 12. Similarly, the arcus tendineus fascia pelvis 10 extends from the ischial spine 13 to the insertion of the arcus tendineus fascia pelvis in the pelvic bone portion 1b, at 14.

The urethra 4 is additionally supported by a pair of pubourethral ligaments 15 and 16. Pubourethral ligament 15 is attached to the side of urethra 4 and extends forwardly to the pubic bone 1a adjacent the insertion 12 of the arcus tendineus fascia pelvis 9. In a similar fashion, the pubourethral ligament 16 extends from the opposite side of the urethra 4 to the pubic bone 1b adjacent the insertion 14 of the arcus tendineus fascia pelvis 10. The attachment of the pubourethral ligaments to the sides of urethra 4 are located at the above-noted intermediate 60 percent of the urethra.

From the above, it will be apparent that weakening of the endopelvic fascia 8, weakening of the anterior vaginal wall 6a, weakening of the attachments to the pubic bone and stretching of the pubourethral ligaments 15 and 16 can result in urethral hyper-mobility and incontinence. The sling of the present invention not only supports the normal urethral suspensistory mechanism, but also limits urethral descent at the site of continence control. Since the urethra cannot be elevated above the level of attachment of the sling to the inferior/posterior border of the pubis, it functions only with increasing intraabdominal pressure to prevent urethral descent.

Figure 4:
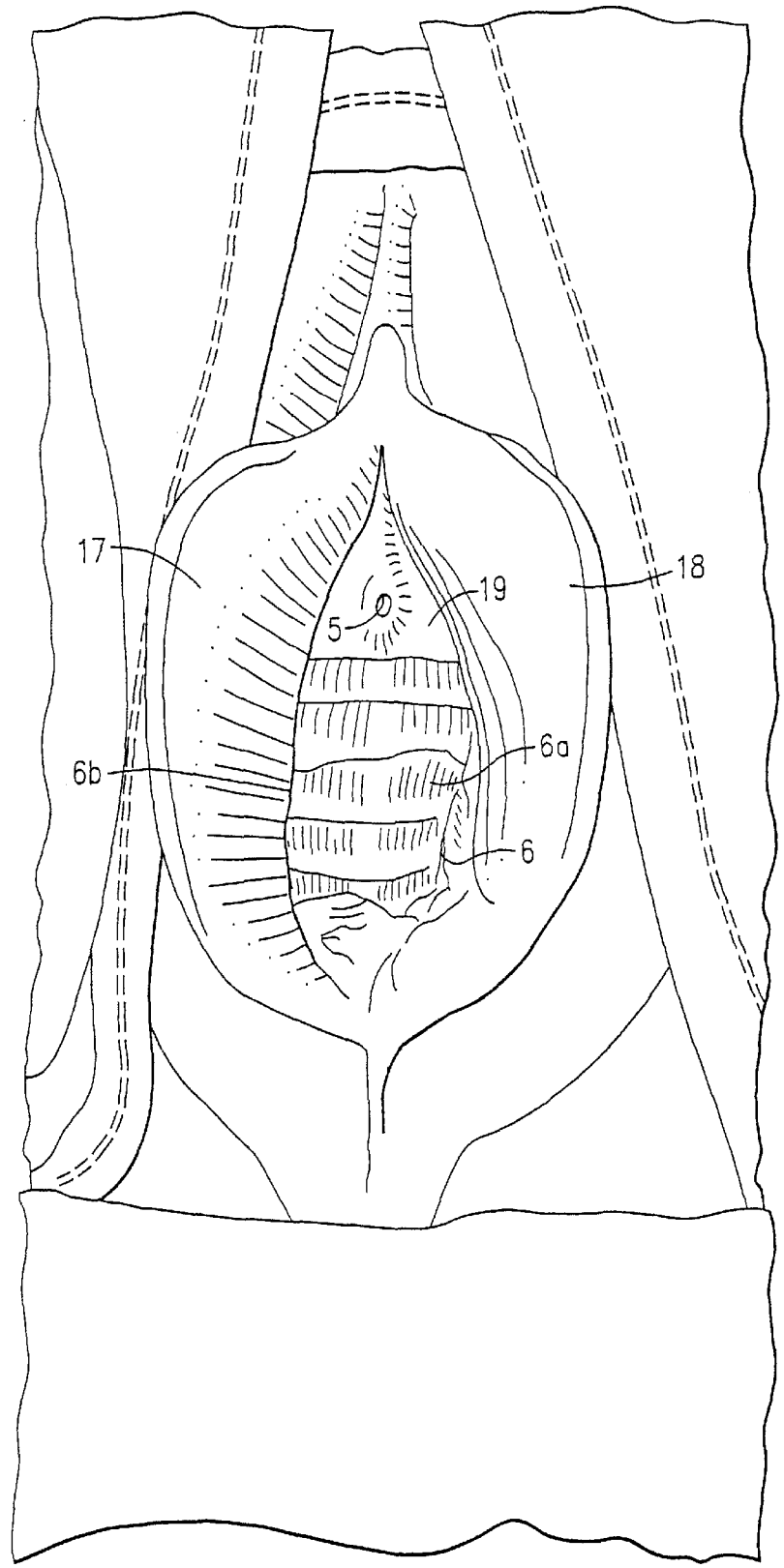
FIG. 4 is a frontal surgical view of the external female genitalia in surgical preparation with the labia minora in open position exposing the vestibule and the lower vagina of a female patient having the prolapse condition illustrated in FIG. 3.

At this point, the manner in which the system of the present invention is applied and used will now be described. Reference is first made to FIG. 4 which is a frontal or surgical view of the female genitalia with the labia minora 17 and 18 parted to reveal the urethral meatus 5 and the vestibule 19. The opening of the vagina 6 is shown at 6b. The anterior wall 6a of the vagina is also shown. Prolapse of the bladder, the urethra and the anterior wall 6 of the vagina is evidenced by a bulging of the vagina (as shown) and the fact that the anterior wall 6a falls away less steeply than would be the case in a healthy woman. Depending upon the severity of the prolapse, the anterior wall 6a of the vagina may extend through the vaginal opening 6b.

Figure 5:
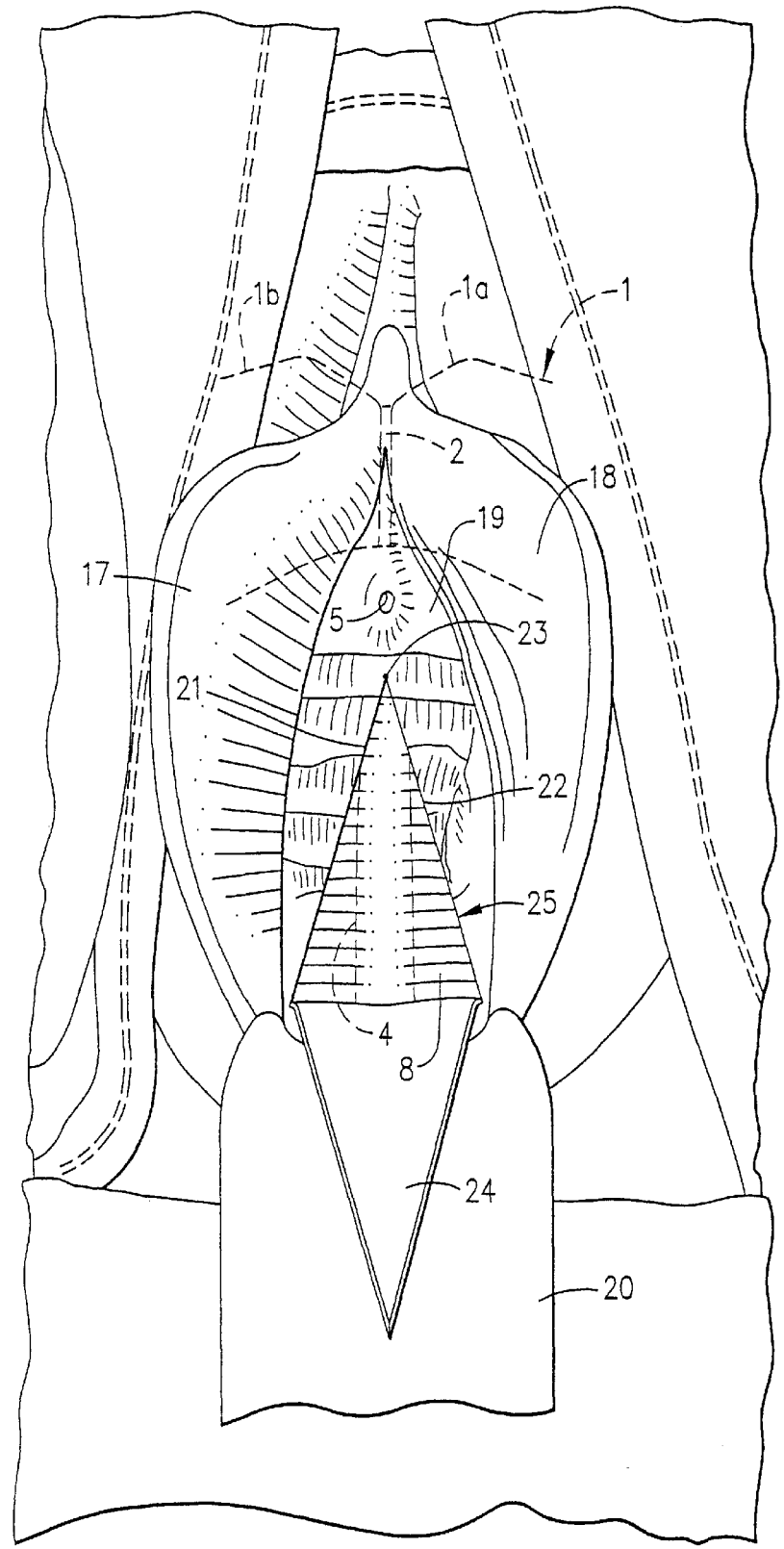
FIG. 5 is a fragmentary surgical view, similar to FIG. 4, and illustrates the posterior orifice of the vagina distended by means of a vaginal retractor, together with an incision made in the anterior wall of the vagina exposing the fascia tissue covering the urethra.

Reference is now made to FIG. 5. In this figure the posterior wall of the vagina and the adjacent portion of the vaginal opening 6b are distended by means of a vaginal retractor 20. A pair of divergent incisions 21 and 22 is made, beginning at posterior urethral fold, indicated at 23. That portion 24 of the anterior vaginal wall 6 between the incisions 21 and 22 is carefully separated from the endopelvic fascia 8 forming a triangular flap 24. The vaginal wall flap 22 can be used as a tractor to pull the operative field into better view. With the flap 22 in the position shown, it will be noted that a triangular incision, generally indicated at 25, results.

While incisions of other configurations can be used, the above described triangular incision 25 has certain advantages. First of all, the vaginal wall edges may be trimmed of excess material having been stretched by prolapse. Furthermore, the endopelvic fascia has been left intact with minimal damage to the local nerve supply to the urethra and bladder, and with little damage to the blood supply of the endopelvic fascia.

Figure 6:
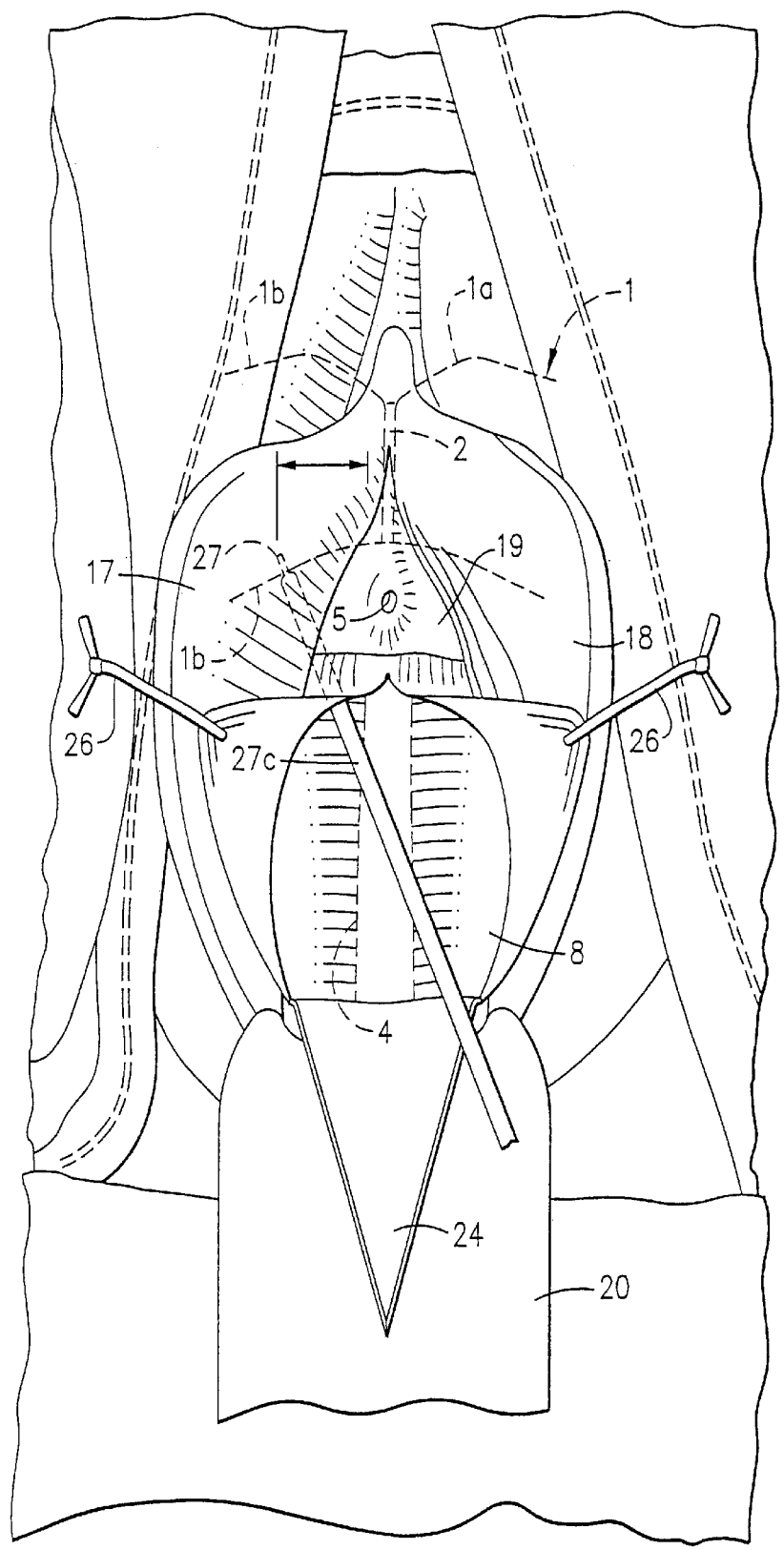
FIG. 6 is a fragmentary surgical view similar to FIG. 5 and illustrates the lateral edges of the incision stretched in open position and the placement of a suture-bearing anchor screw retropubically at the posterior/inferior border of the pubic bone to the left of the pubic symphysis and within 1 to 2 mm from the insertion of the arcus tendineus fascia pelvis.

The endopelvic fascia attachment to the vaginal epithelium having been separated, the incision 25 may be stretched to a more open position and held in that position by retractors, or temporary stitches engaging the adjacent drape, as shown at 26 in FIG. 6. At this point, dissection is carried out laterally to assess the integrity of the lateral attachment of the endopelvic fascia to each arcus tendineus fascia pelvis 9 and 10. Evaluation is made by palpation and direct visualization. Repairs by suturing may be made, if required. These sutures are left untied until the system of the present invention is in place. Additional repairs may also be made, if required.

The system of the present invention can now be put in place. To this end, a pair of pubic bone anchor screws are located in the pubic bone portions 1a and 1b. In FIG. 6, an anchor screw 27 is shown being drilled in place in the pubic bone portion 1b. The site of the pubic bone anchor screw 27 is determined by palpating the course of the arcus 10 (see FIG. 2) from the ischial spine 13 to the arcus insertion 14 into the posterior/inferior aspect of pubic bone portion 1b. The anchor screw 27 is provided with a pair of sutures 27a and 27b affixed thereto. The anchor screw 27 and its sutures 27a and 27b are located within a driver 27c which, in turn, may be mounted in a surgical drill (not shown). A non-limiting example of such an anchor screw and driver is taught in U.S. Pat. No. 4,632,100. With respect to the sutures 27a and 27b, excellent results have been achieved with permanent 0 sutures manufactured by Ethicon, Inc. of Summerville, N.J. and sold under the registered trademark Mersilene®.

Figure 7:
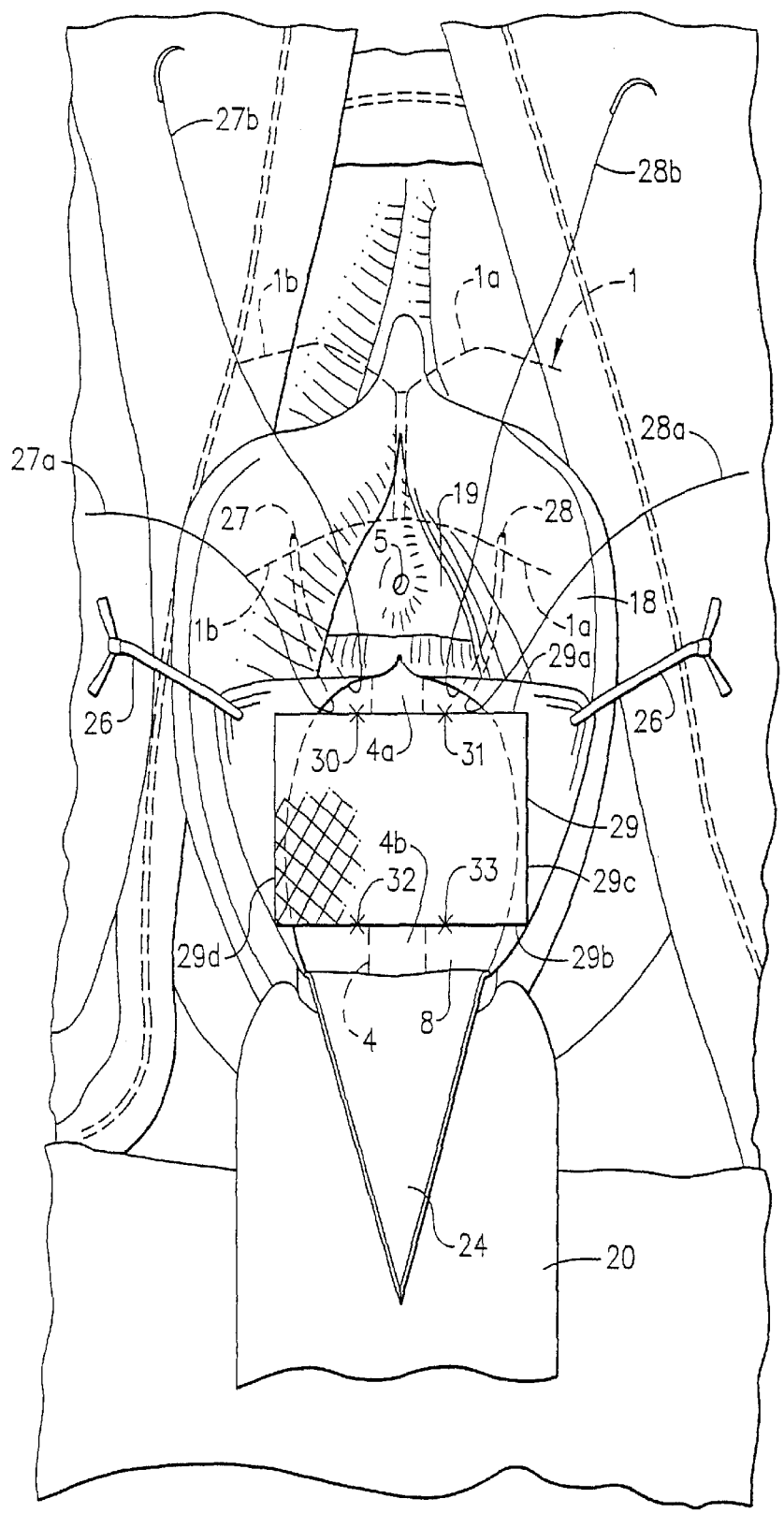
FIG. 7 is a fragmentary surgical view, similar to FIG. 6, and illustrates both suture-bearing anchor screws in place in the pubic bone and a rectangular piece of surgical mesh overlying the urethra and sutured adjacent either side of the urethra to the endopelvic fascia.

Anchor screw 27 is placed approximately one fingerbreadth laterally of the urethra 4 and approximately 1 cm laterally of the symphysis pubis 2. The anchor screw 27 is then directed to the retropubic area approximately 0.5 cm posteriorly and superiorly from the inferior edge of the ischial ramus. Once located, the anchor screw 27 is driven into the pubic bone and is set. The sutures 27a and 27b are temporarily laid aside as is shown in FIG. 7. It will be understood that a second anchor screw 28 will be attached to the pubic bone portion 1a in precisely the same manner and at the corresponding position on the pubic bone portion 1a. This is shown in FIG. 7. The anchor screw 28 is provided with a pair of sutures 28a and 28b which are laid aside as shown in FIG. 7.

A substantially rectangular patch 29 of surgical mesh, approximately 3 cm wide and 6 cm long is then provided. Excellent results have been achieved by using a surgical mesh manufactured by Ethicon, Inc. of Summerville, N.J. and sold under the registered trademark Mersilene®. The surgical mesh patch is shown in FIG. 7 at 29. The patch is provided with longitudinal edges 29a and 29b and transverse edges 29c and 29d. The mesh 29 is laid upon the endopelvic fascia 8 with its longitudinal edges 29a and 29b extending transversely of the urethra 4 beneath the endopelvic fascia 8. Four permanent sutures are used to transfix the mesh 29 along the lateral borders of the urethra at the edges 29a and 29b of mesh 29. These sutures are shown at 30, 31, 32 and 33 in FIG. 7. The sutures are so positioned as to allow a slight trough-like space between the mesh 29 and the endopelvic fascia 8 and urethra 4. This trough-like space prevents undue tension on the urethra by the mesh, when the mesh is formed into a sling, as will be apparent hereinafter. Excellent results were achieved when the sutures 30–33 constituted permanent 000 sutures manufactured by Ethicon, Inc. of Summerville, N.J. and sold under the registered trademark Ethibond®. It will further be noted in FIG. 7 that the mesh 29, from longitudinal edge 29a to longitudinal edge 29b extends along the above-described intermediate 60% of the length of the urethra 4, as indicated by the points 4a and 4b shown in FIG. 7.

Figure 8:
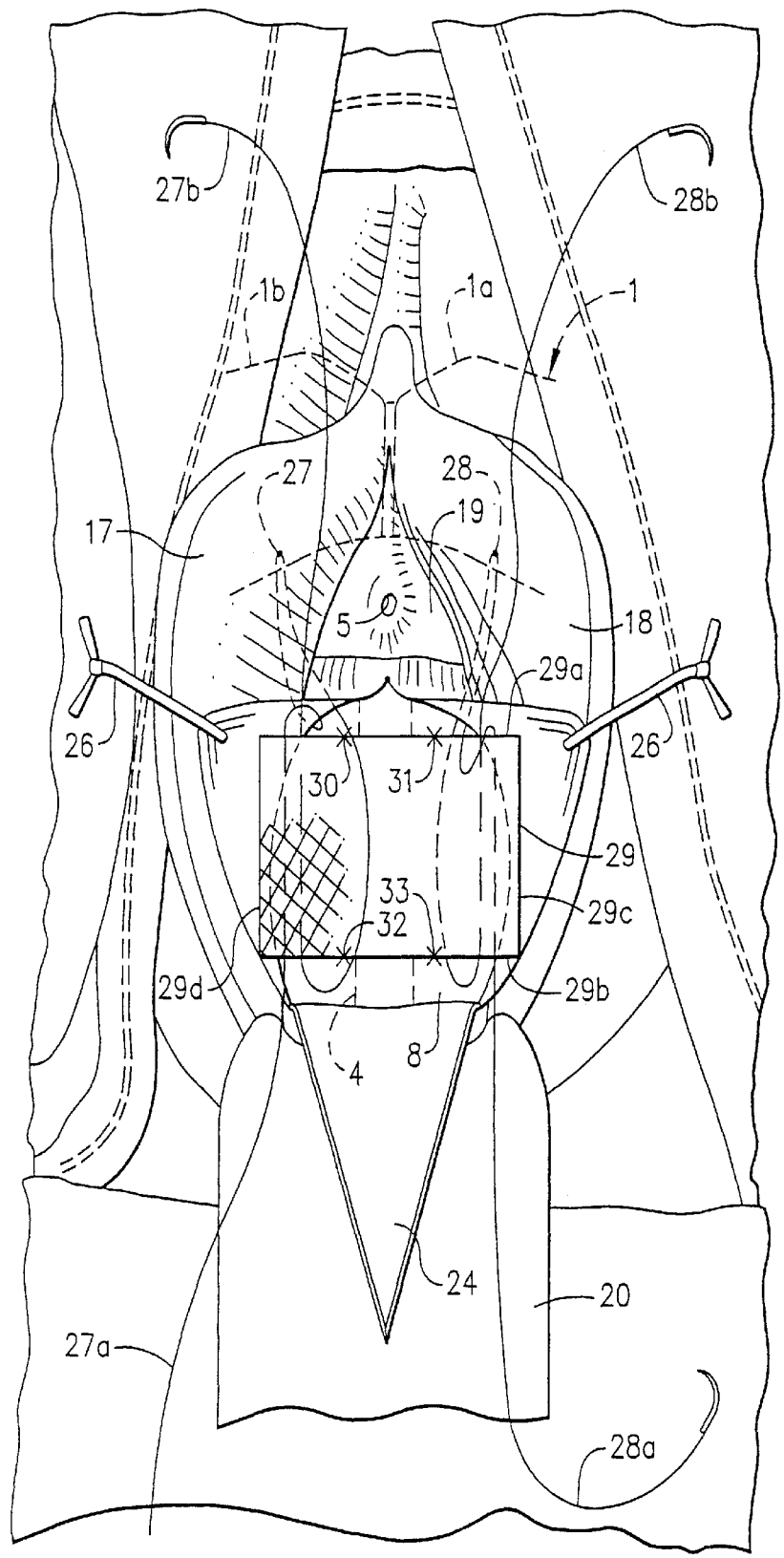
FIG. 8 is a fragmentary surgical view, similar to FIG. 7, and illustrates the sutures of each anchor screw oppositely threaded through its respective side of the mesh.
Figure 9:
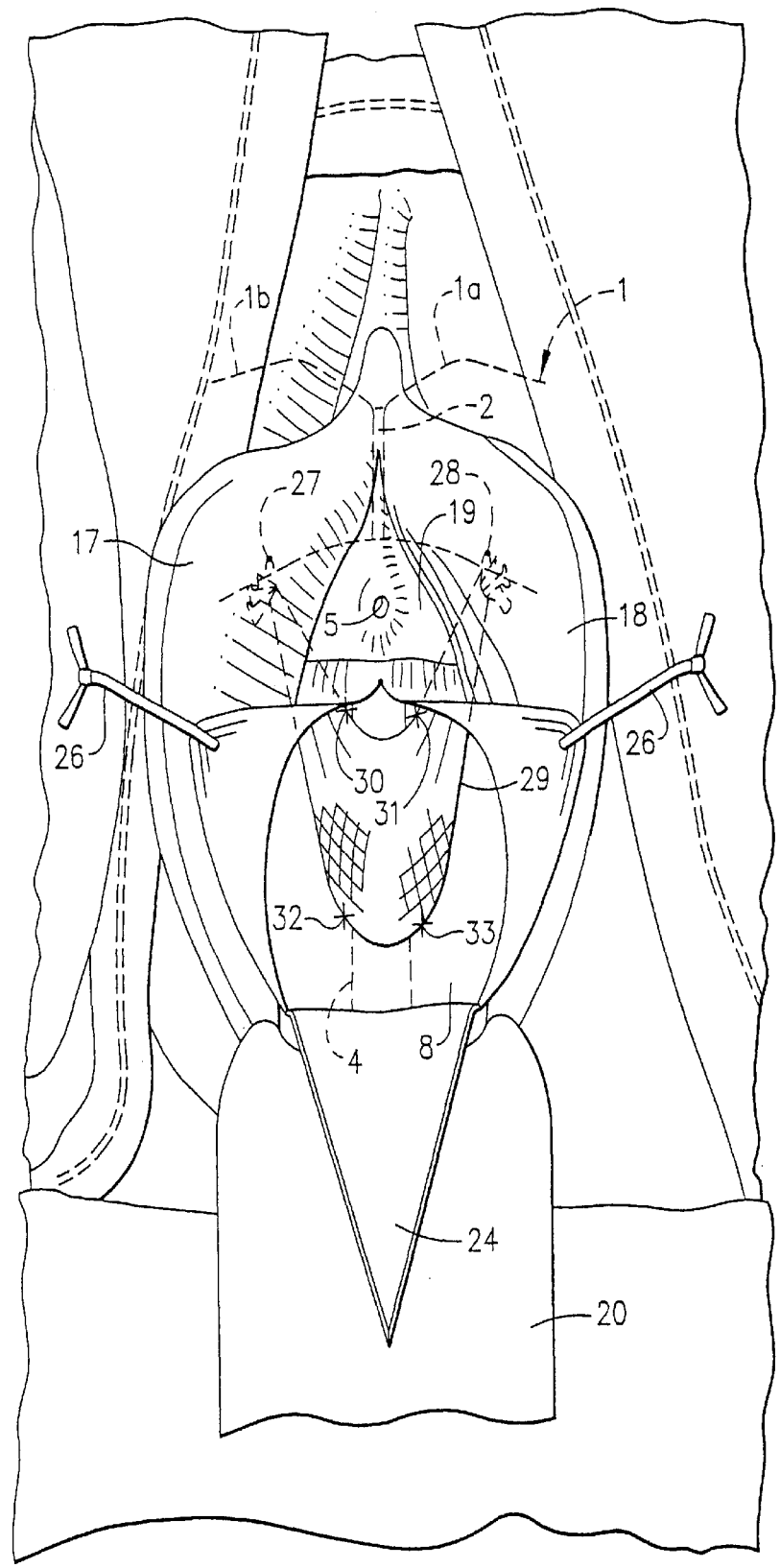
FIG. 9 is a fragmentary surgical view, similar to FIG. 8 and illustrates the anchor screw sutures being tensioned and tied, bringing the lateral edges of the mesh into conjunction with the anchor screws, forming a sling support for the urethra.
Figure 10:
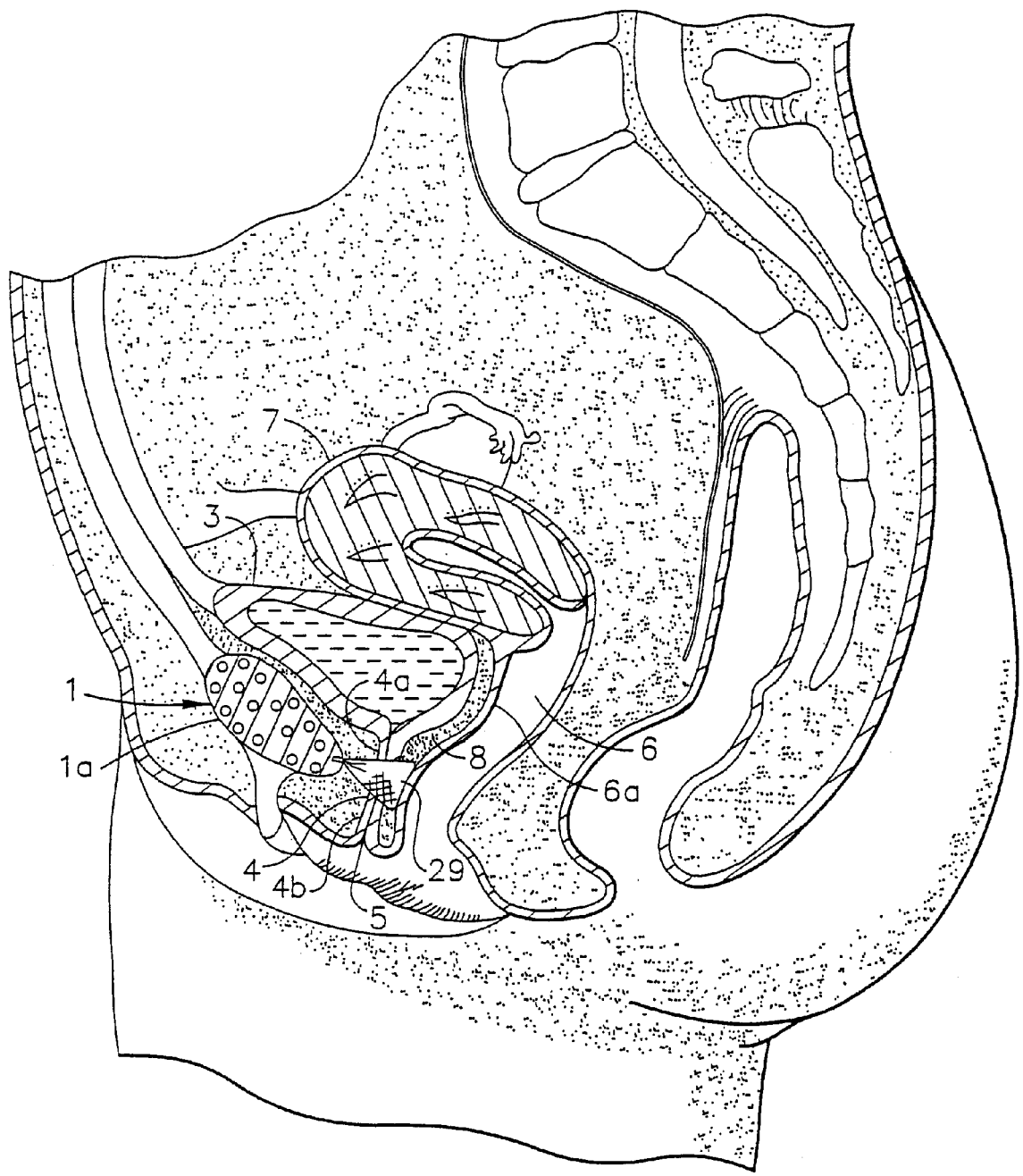
FIG. 10 is a fragmentary midsagittal cross-sectional view, similar to FIG. 1, and illustrates the urethra, bladder and neighboring organs of a woman whose urinary prolapse has been corrected by the system of the present invention.

Reference is now made to FIG. 8. In this figure, it is shown that the permanent sutures 27a and 27b of anchor screw 27 are woven transversely of the mesh 29 in opposite directions between the longitudinal mesh edges 29a and 29b, and inset from the transverse mesh edge 29d. In a similar fashion, the sutures 28a and 28b are woven transversely of mesh 29 in opposite directions between the longitudinal edges 29a and 29b of the mesh, and inset from the transverse mesh edge 29c. The placement of the anchor sutures through the mesh is determined by placing upward tension on the mesh under cystoscopic guidance to determine the approximate tension required for urethral coaptation from each end of the mesh. As is shown in FIGS. 9 and 10, the sutures 27a and 27b and sutures 28a and 28b are tied in a bilateral fashion to their respective points of attachment to the pubic bone portions 1a and 1b. This causes the mesh 29 to be transformed into a sling.

Thereafter, the repair sutures for attaching the endopelvic fascia to the arcus tendineus fascia pelvis 9 and/or 10 are tied sequentially. Any mid-line or transverse defects are noted and repaired. Additional repairs may be made depending upon the requirement of the individual patient. Then, the triangular flap 24 is removed and the cut edges of the anterior vaginal wall are approximated with absorbable 00 polyglycolic sutures in a running fashion. At this point, the cul-de-sac and posterior vaginal segment defects are repaired. Cystoscopic examination of the urethra and the urethral orifices with indigo carmine dye are performed. Bladder drainage is provided by a suprapubic cystotomy.

Prior art incontinence procedures involving the use of a sling have enjoyed excellent surgical success rates. They have, on the other hand, been plagued with numerous drawbacks including voiding dysfunction, urinary retention, detrusor instability, infection, and erosion of the sling material. A number of these problems are, in all likelihood, related to difficulty in achieving the proper tension of the sling.

Figure 11:
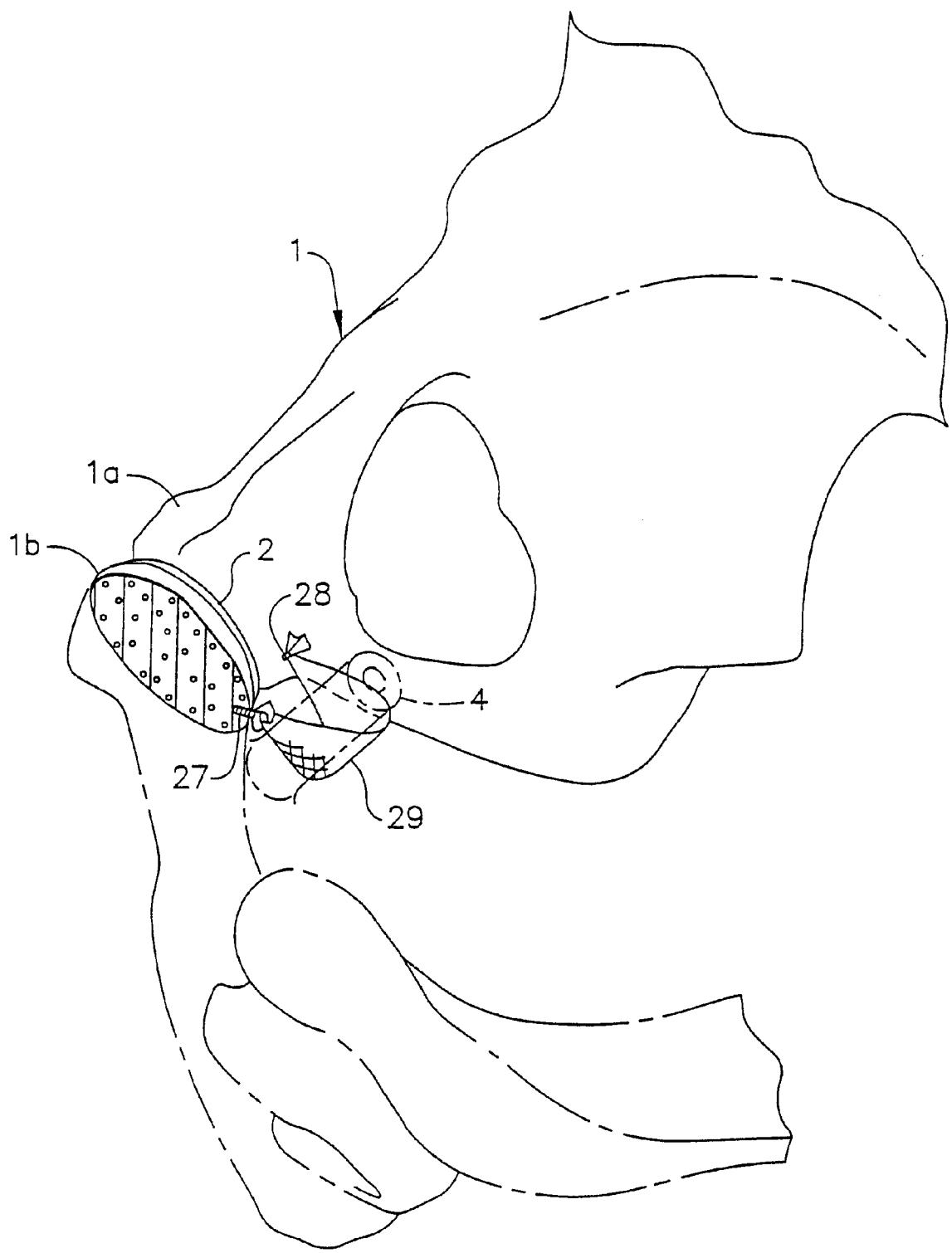
FIG. 11 is a fragmentary view of the pubic bone and the urethra, the urethra being supported by the system of the present invention.

The system of the present invention (i.e. the anchor screws 26 and 28 and their placement, the sutures 26a, 26b, 28a and 28b and the sling 29 and its placement) is characterized by a number of advantages (see FIG. 11). It is generally believed (as indicated above) that urethral hypermobility is caused by deficiencies in the arcus tendineus fascia pelvis and the pubourethral ligaments. In addition, the pubourethral ligaments are subject to stretching or elongation. None of these damaged, or elongated, or deficient muscular and fascial paraurethral tissues is used to supply the support and stabilization provided by the system of the present invention. The system of the present invention does not hyperelevate the urethra (see FIG. 10) by attachment to the superior border of the pubis, to Cooper's ligament or to the rectus abdominus fascia. It is to be noted that in the normal continent female, the urethral position is never found to be hyperelevated (see FIG. 1). By suturing the mesh sling of the present invention to anchor screws located, as described above, to either side of the symphysis pubis in the retropubic area posteriorly and at about 0.5 cm superiorly of the inferior edge of the ischial ramus, such hyperelevation is precluded. The sutures that connect the mesh sling to the anchor screws are, themselves, short which not only assists in developing the proper tension, but also minimizes lateral movement cause by intraabdominal pressure. Such movement is characteristic of long length sutures. In addition, it will be noted that the sling of the present invention differs from the pubourethral ligaments primarily in that the sling passes about and behind the urethra, rather than being attached to the urethra sides. However, sutures 30 through 33 simulate an attachment to the urethra sides. Those portions of the sling between each anchor and its respective pair of sutures 30–32 and 31–33 bear most of the support load and closely simulate the pubourethral ligaments. As a result of this, the sling not only serves much the same purpose as the pubourethral ligaments, but also serves much the same purpose as the endopelvic fascia and the anterior vaginal wall in a healthy woman. The sling engages the urethra and stabilizes it by passing about the above-described intermediate 60 percent of the urethra, believed to be the primary continence control portion of the urethra. It has been found that repair of other site-specific defects of genital prolapse corrects only those defects and does not alter the incontinence mechanism. For example, paravaginal repairs of the endopelvic fascia from one arcus to the other can only be expected to correct the protrusion causing a cystourethrocele. If the pubourethral ligaments are damaged, their ability to limit urethral descent with increasing intraabdominal pressures will remain impaired no matter how tight the endopelvic fascia is stretched from one arcus to the other.

Finally, the procedure of the present invention is a relatively simple one and, as indicated above, proper tension on the sling is far easier to determine than in prior art procedures.

The present invention has been described in the terms of vaginal installation of the system of the present invention. At this time, this is the preferred procedure. Nevertheless, it will be understood that the system of the present invention could be installed abdominally or laproscopically.

Figure 12:
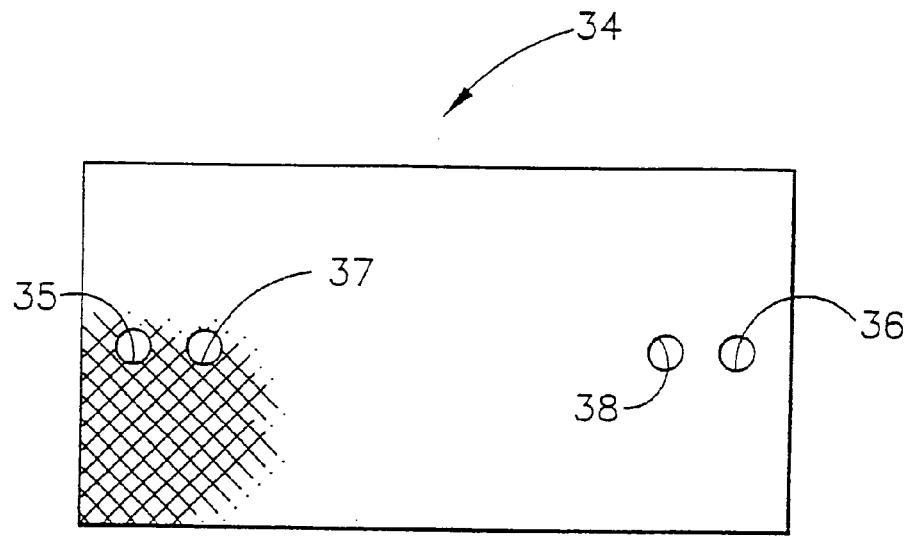
FIG. 12 is an elevational view of another embodiment of a surgical mesh sling.

Reference is now made to FIG. 12 which illustrates another embodiment of the surgical mesh member which serves as a urethral sling. The mesh member is generally indicated at 34 and preferably is made of the same material described with respect to the surgical mesh member 29 of FIG. 7. The surgical mesh member 34 is provided with a pair of holes 35 and 36. The holes 35 and 36 are sized to just nicely receive the shanks of headed surgical anchor screws.

The procedure for installing the surgical mesh member 34 is substantially identical to that described with respect to surgical mesh member 29, with the exception that surgical mesh member 34 is not tied to anchors by sutures. Surgical mesh member 34 is provided with four permanent sutures equivalent to sutures 30–33 of FIG. 7 whereby it is attached to the endopelvic fascia 8. Again, the sutures are so positioned as to allow a slight trough-like space between the mesh 34 and the endopelvic fascia 8 and urethra 4. As indicated with respect to sutures 30–33 of FIG. 7, this trough-like space prevents undue tension on the urethra by the mesh, when the mesh is formed into a sling.

An anchor screw (not shown) is caused to have its shank inserted through hole 35 in mesh member 34 and is located in the posterior/inferior aspect of the pubic bone portion 1a. The site of the anchor screw is determined in exactly the same manner as that described with respect to anchor screw 27 of FIG. 7. In a similar fashion, the shank of a second headed anchor screw is passed through the hole 36 in mesh member 34 and is located in the posterior/inferior aspect of pubic bone portion 1b.

Preferably, mesh member 34 is provided with more than one pair of holes. In this way, the surgeon can select an appropriate pair of holes to achieve the best placement of the gauze member sling 34 when it is attached to the posterior/inferior aspect of the pubic bone portions 1a and 1b. To this end, mesh member 34 is shown having a second pair of holes 37 and 38.

Preferably, the holes 35–38 are provided with reinforced stitching about their edges in a manner somewhat similar to button holes.

Figure 13:
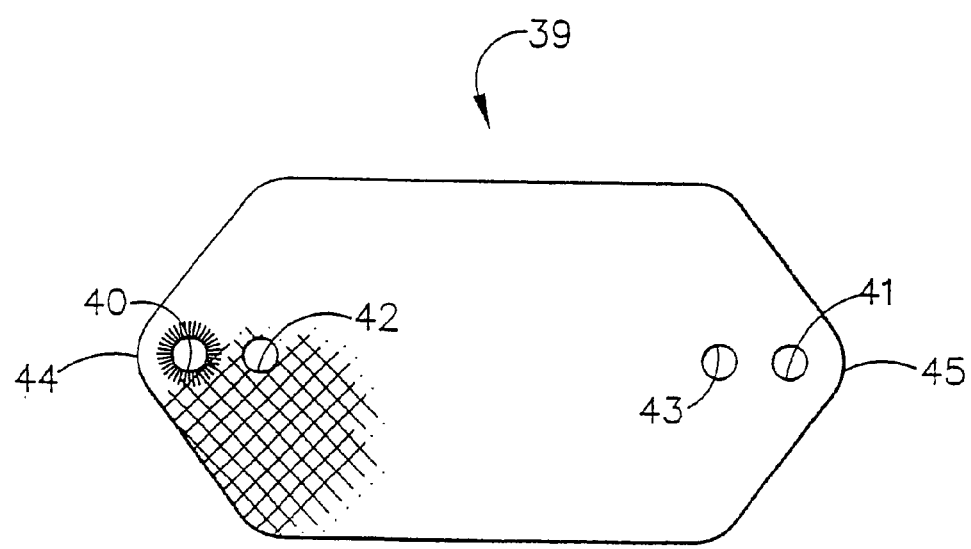
FIG. 13 is an elevational view of yet another embodiment of a surgical mesh sling.

It is within the scope of the invention to shape the ends of the mesh member. This is illustrated in FIG. 13 wherein the mesh member 39, having a first pair of holes 40–41 and a second pair of holes 42–43, is provided with somewhat pointed ends 44 and 45. It will be understood that the ends may be otherwise shaped. For example, they could be arcuate or rounded.

The mesh sling elements 34 and 39 of FIGS. 12 and 13 tend to simplify the surgical procedure since it is no longer necessary to weave pairs of sutures transversely of the mesh member ends as shown in FIG. 8, and to tie these sutures as shown in FIG. 9. The number of pairs of holes in the mesh elements 34 and 39 does not constitute a limitation of the present invention. Excellent results can be achieved using gauze elements 34 or 39 having a length of about 6 centimeters and a width of about 3 centimeters.

As used herein and in the claims such works as "uppermost", "lowermost", "right", "left", and the like are used in conjunction with the drawings for clarity.

Modifications may be made in the invention without departing from the spirit of it. For example, throughout the specification, the sling of the present invention has been described as a mesh sling. It will be understood by one skilled in the art that the sling could also be made of autologous fascia or cadaveric fascia.

Furthermore, while the system and method of the present invention are described in their application to women, they could also be applied to men, as well.

What is claimed is:

1. A method of treating urinary incontinence in a patient comprising:
    preparing said patient for surgery;
    creating an incision allowing access to the urethra;
    introducing a mesh material through said incision and moving said mesh to a position that traverses the urethra;
    adjusting the position and tension of said mesh material relative to said urethra through manipulation of at least one suture interlaced within a weave of said mesh material;
    securing said mesh material into place in a manner to effectively treat the urinary incontinence; and,
    closing said incision.

2. A method according to claim 1, wherein said incision is created in the vagina of a female patient.

3. A method according to claim 1, wherein said suture is interlaced into said mesh material just prior to the adjusting of the position and tension of the mesh material.

4. A method according to claim 1, wherein the adjusting of the position and tension of the mesh material is performed by placing upward tension on said mesh material.

5. A method according to claim 1, wherein the manipulation of at least one suture is performed with a suture that is interlaced along substantially the length of one side of said mesh material.

6. A method according to claim 1, wherein the securing of said mesh material includes the manipulation of sutures located proximal to the urethra and distal from ends of the mesh material.

7. A method according to claim 1, wherein the securing of said mesh material includes connecting ends of said mesh material to bone anchors located in a pubic bone of said patient.

8. A method of treating urinary incontinence in a patient comprising:
    identifying a region on the patient for making an incision;
    creating an incision allowing access to the urethra;
    observing the tissue revealed by said incision,
    introducing a mesh material through said incision and moving said mesh to a position that traverses the urethra;
    manipulating said mesh material using at least one suture interlaced within said mesh material until opposite ends of said mesh material extend upwardly toward an abdomen of said patient;
    checking the condition of said urethra in order to confirm proper manipulation of said mesh material; and,
    repairing said incision.

9. A method according to claim 8, wherein the introduction of said mesh material is performed through the vagina of a female patient.

10. A method according to claim 8, wherein the manipulation of said mesh material is performed through the abdomen of said patient.

11. A method according to claim 8, wherein said suture is interlaced into said mesh material just prior to the manipulation of the mesh material.

12. A method according to claim 8, wherein the manipulating of said mesh material is performed by placing upward tension on said mesh material.

13. A method according to claim 8, wherein the manipulation of said mesh material using at least one suture is performed with a suture that is interlaced along substantially the length of one side of said mesh material.

14. A method according to claim 8, wherein the securing of said mesh material includes the manipulation of sutures located proximal to the urethra and distal from ends of the mesh material.

15. A method according to claim 8, wherein the checking of the condition of the urethra includes cystoscopic observation of the urethra.

16. A method of treating urinary incontinence in a patient comprising:
    identifying a region on a patient for performing surgery,
    creating an incision allowing access to the urethra;
    introducing a mesh material through said incision and moving said mesh to a position that traverses the urethra;
    observing the mesh material at said position; and,
    adjusting the position of said mesh material relative to said urethra using a suture that is attached to said mesh material in a manner so as to minimize undesirable cinching of said mesh material during permanent placement of said mesh material in said patient.

17. A method according to claim 16, wherein said incision is created in the vagina of a female patient.

18. A method according to claim 16, wherein the adjusting of the position of said mesh material is performed using a suture that is interlaced into said mesh material.

19. A method according to claim 18, wherein said suture is interlaced into said mesh material just prior to the adjusting of the position of said the mesh material.

20. A method according to claim 18, wherein the adjusting of the position of said mesh material is performed using a suture that is interlaced along substantially the length of one side of said mesh material.

21. A method according to claim 18, wherein said suture is interlaced into said mesh material just prior to the adjusting of the position of said the mesh material.

22. A method of treating urinary incontinence in a patient comprising:
    identifying a patient suffering from urinary incontinence;
    identifying a region on said patient for performing surgery;
    creating an incision allowing access to a urethra;
    introducing a mesh material through said incision and moving said mesh to a position that traverses the urethra; and,
    controlling tension of said mesh material relative to the urethra through manipulation of sutures that are attached to said mesh material at locations spaced from each distal end of said mesh material and on both sides of a central region of said mesh material; and,
    evaluating the state of said mesh material after controlling the tension.

23. A method as set forth in claim 22, wherein the controlling of tension is performed using permanent sutures.

24. A method as set forth in claim 22, wherein the creating of said incision is performed through the vagina of a female patient.

25. A method as set forth in claim 22, wherein the introducing of a mesh material is performed through the abdomen.

26. A method as set forth in claim 22, wherein the evaluating of the state of said mesh material is performed using cystoscopy.

27. A method as set forth in claim 22, wherein the controlling of the tension is performed so as to secure the mesh material relative to said urethra.

28. A method of treating urinary incontinence in a patient comprising:
    identifying a patient suffering from urinary incontinence;
    exposing a urethra of said patient;
    inserting a urethral support material into said patient;
    manipulating said urethral support until said urethral support is located beneath said urethra at a position most effective for treating the incontinence; and,
    ensuring said urethral support is located at a position most effective for treating the incontinence by controlling the tension of regions of said urethral support that are in near proximity to said urethra; and,
    closing the exposure to said urethra.

29. A method as set forth in claim 28, wherein the ensuring of urethral support is performed using sutures.

30. A method as set forth in claim 29, wherein the ensuring of urethral support is performed using permanent sutures.

31. A method as set forth in claim 28, wherein the exposing of said urethra is performed through the vagina of a female patient.

32. A method as set forth in claim 28, wherein the evaluating of the state of said mesh material is performed using cystoscopy.

33. A method as set forth in claim 28, wherein the ensuring of urethral support includes securing the mesh material relative to the urethra.

34. A method of treating urinary incontinence in a patient comprising:
    identifying a location on a patient for performing surgery;
    creating an incision allowing access to the urethra;
    introducing a mesh material through said incision and moving said mesh to a position that traverses the urethra;
    manipulating said mesh material until opposite ends of said mesh material extend upwardly toward an abdomen of said patient;
    ensuring against undue pressure of said mesh material relative to said urethra by controlling the tension of said mesh material at a region proximal to opposite sides of said urethra; and,
    closing said incision.

35. A method according to claim 34, wherein the ensuring against undue pressure includes controlling the tension of said mesh material using at least one suture.

36. A method according to claim 35, wherein the at least one suture is a permanent suture.

37. A method as set forth in claim 34, wherein the creating of said incision is performed through the vagina of a female patient.

38. A method as set forth in claim 34, including evaluating of the state of said mesh material after ensuring against undue pressure.

39. A method as set forth in claim 34, wherein the controlling of the tension is performed so as to secure the mesh material relative to said urethra.

* * * * *